(12) United States Patent
Kulkarni et al.

(10) Patent No.: US 7,282,218 B2
(45) Date of Patent: Oct. 16, 2007

(54) PH SENSITIVE POLYMER FOR INHIBITING TRANSFORMATION IN DRUGS

(75) Inventors: Mohan Gopalkrishna Kulkarni, Maharashtra (IN); Anupa Ramesh Menjoge, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 611 days.

(21) Appl. No.: 10/739,528

(22) Filed: Dec. 19, 2003

(65) Prior Publication Data

US 2005/0136115 A1   Jun. 23, 2005

(51) Int. Cl.
*A61K 9/14* (2006.01)

(52) U.S. Cl. ...................................................... 424/487

(58) Field of Classification Search ................ 424/487, 424/483, 472
See application file for complete search history.

(56) References Cited

U.S. PATENT DOCUMENTS

| | | | |
|---|---|---|---|
| 3,608,063 A * | 9/1971 | Banker ........................ 424/485 |
| 4,786,508 A * | 11/1988 | Ghebre-Sellassie et al. 424/482 |
| 5,116,603 A * | 5/1992 | Friedman ..................... 424/53 |
| 5,286,489 A | 2/1994 | Tsau et al. |
| 5,445,830 A | 8/1995 | Ishizue et al. |
| 6,372,259 B1 * | 4/2002 | Kumar ........................ 424/497 |
| 6,797,768 B2 * | 9/2004 | Lyons ......................... 524/561 |
| 2003/0064108 A1 * | 4/2003 | Lukas et al. ................. 424/495 |
| 2003/0220413 A1 | 11/2003 | Petereit et al. |
| 2005/0136114 A1 * | 6/2005 | Kulkarni et al. ............. 424/486 |
| 2005/0137372 A1 * | 6/2005 | Kulkarni et al. ............. 526/319 |
| 2005/0281874 A1 * | 12/2005 | Menjoge et al. ............. 424/472 |
| 2006/0134054 A1 * | 6/2006 | Kulkarni et al. ......... 424/70.16 |
| 2006/0141053 A1 * | 6/2006 | Menjoge et al. ............. 424/490 |

FOREIGN PATENT DOCUMENTS

| | | |
|---|---|---|
| EP | 0781551 A1 | 7/1997 |
| EP | 1317925 A1 | 6/2003 |

* cited by examiner

*Primary Examiner*—Sharon E. Kennedy
(74) *Attorney, Agent, or Firm*—Nixon & Vanderhye P.C.

(57) ABSTRACT

The present invention discloses a substantially amorphous pharmaceutical composition comprising a drug that can exist in a variety of polymorphic forms and a pH sensitive polymer, which inhibits the crystallization of the drug during formulation and reconstitution. Polymers of higher molecular weight are more effective at lower loading, especially when the drug polymer matrix is prepared by the solvent evaporation or solvent extraction technique. The compositions used as dry syrups maintain bioavailability of the drug and effectively mask the taste of the drug when the composition is reconstituted.

42 Claims, 15 Drawing Sheets

PH SENSITIVE POLYMER FOR INHIBITING TRANSFORMATION IN DRUGS

FIELD OF INVENTION

Figure 1:
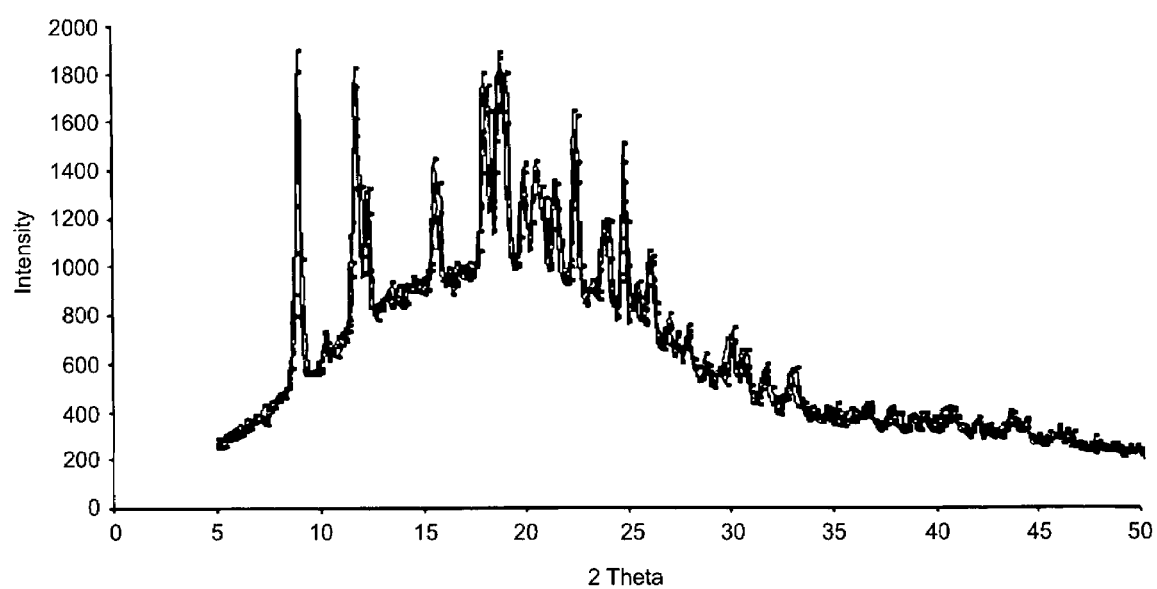

The present invention relates to taste masked compositions comprising a bitter drug and a pH sensitive polymer, which maintain the drug in substantially amorphous form and enhances bioavailability of the drug and further a method of preparing the same.

BACKGROUND OF THE INVENTION

Although a variety of delivery systems are being developed for different routes of administration like oral, parenteral, nasal and transdermal, etc. the oral route remains attractive because this mode of administration is an easy, convenient, noninvasive and familiar method of drug delivery. The majority of prescribed drugs are designed for oral application since they can be self-administered by the patient without hospitalization. Oral dosage forms are designed according to the nature of the drug, the nature of application and the need for any special effects as desired in the delivery system. The common oral dosage forms include: liquid mixtures like solutions, suspensions, solid dosage forms like tablets and capsules and liquid filled capsules etc. The solid dosage forms are further modified depending on the therapeutic action desired like controlled, extended or delayed release. However, patients at the extremes of age, such as children and the elderly, often experience difficulty in swallowing solid oral dosages forms. For these patients the drugs are mostly provided in liquid dosage forms such as solutions, emulsions and suspensions. These dosage forms usually lead to perceptible exposure of the active drug ingredient to the taste buds, which is a very serious problem when the drug has an extremely unpleasant or bitter taste.

The bitter taste of the drugs, which are orally administered, is disadvantageous in several aspects. Taste is an important parameter governing the compliance. The disagreeable taste of drugs causes difficulties in swallowing or causes patients to avoid their medication, thereby resulting in low patient compliance. Conventional taste masking techniques such as use of sweeteners, amino acids, flavoring agents are often unsuccessful in masking the taste of the highly bitter drugs like quinine, barberin, etoricoxib, antibiotics like levofloxacin, ofloxacin, sparfloxacin, gatifloxacin, ciprofloxacin, cefuroxime axetil, erythromycin and clarithromycin. Thus taste-masking technologies are considered important and are developed by many researchers.

Taste masking is a major problem when the drugs are extremely unpleasant and bitter. Further, this problem is not only restricted to the liquid oral compositions like solutions, dry syrups and suspensions but may also be encountered during the formulation of chewable tablets or dispersible tablets wherein these dosage forms usually lead to perceptible exposure of active ingredient to taste buds.

The main scientific difficulties associated with oral drug delivery apart from taste masking, relate to a variety of changes the active ingredient undergoes during formulation process and also due to the physicochemical environment that these active ingredients encounter when ingested e.g. the low pH of stomach ranging to the high pH of the small intestine, and the effect of these media on the stability, dissolution and bioavailability of the active ingredient. For many drugs the region of the gastrointestinal tract, which provides an effective absorption window, is quite limited. For example, the uptake may be limited to a particular region of the small intestine or limited only to the upper gastric cavity. Some drugs have a tendency to change their polymorphic forms during formulation or in contact of the gastric fluid thereby affecting their bioavailability. The physiochemical properties of the drug affecting the performance of the delivery system are drug solubility, dissolution rate, particle size, lipophilicity, stability and polymorphism and amorphism.

Certain drugs pose challenges during formulation due to their physicochemical characteristics. Cefuroxime axetil exhibits the tendency to gel in contact with the aqueous media necessitating that the dosage form disintegrates into particles rapidly and releases the drug at a faster rate before the gelling occurs in vivo. The amorphous form of cefuroxime axetil exhibits greater bioavailability than the crystalline form. Also the drug shows a tendency to crystallize when in contact with the solvent for long time again making it necessary to dissolve rapidly from the composition. Another problem associated with cefuroxime axetil relates to extremely bitter taste of the drug making it necessary to formulate cefuroxime axetil in a coated delivery system to make it palatable. Celecoxib has an extremely low aqueous solubility and is not readily dissolved and dispersed for rapid absorption in the gastrointestinal tract. Further celecoxib crystals present problems like low bulk density, poor flow characteristics, electrostatic and cohesive properties making it difficult to formulate. The amorphous form of celecoxib exhibits rapid dissolution and also higher bioavailability but it tends to crystallize in contact with the aqueous media. Etoricoxib, another molecule from the COX 2 inhibitor family is also associated with extremely bitter taste. Cefuroxime axetil, a second generation cephalosporin antibiotic and celecoxib, from the class of COX 2 inhibitors both have relatively high dose requirement further increasing difficulty in administering the therapeutically effective dose. Such active molecules which pose formulation problems and are required to be administered as rapid release formulations to overcome the low bioavailability, need a protective polymer coating which releases the active ingredient at a rapid rate without compromising the bioavailability, inhibits the crystallization and also masks the bitter taste of the active ingredient.

Various methods for taste masking have been tried earlier, which include use of ion exchange resins, complexation with pharmaceutically acceptable excipients and coating of drugs by lipids and various polymeric materials. Of these, coating is the most widely used technique for taste masking. Coating of active ingredient can be done by any technique known in the art like microencapsulation, hot melt granulation, wurster coating, spray drying.

One of the approaches for taste masking is the use of ion exchange resins. Various anionic resins like Duolite AP143/1083™ (cholestyramine resin USP), Cationic resin like Amberlite IRP 64™ (copolymer of methacrylic acid crosslinked with divinyl benzene) and Dowex (based on polystyrenesulfonic acid cross linked with divinylbenzene) are used. U.S. Pat. No. 6,514,492, assigned to Schering Plough discloses the use of ion exchange resin AMBERLITE.RTM. IRP 69™ for taste masking of quinolone derivatives thereby eliminating the extreme bitterness of the quinolones in oral liquid formulation.

Patent application WO 01/70194 discloses a fast dissolving orally consumable film adapted to adhere to and dissolve in mouth of the consumer. The film is composed of an ion exchange resin, amberlite and a water soluble polymer pullulan as taste masking agent for the bitter drug, dextromethorphan. The film adheres to the oral cavity and dissolves to deliver the active ingredient. The use of the water soluble polymer in the formulation would restrict the use of such delivery system if the taste masking was desired for liquid oral preparation. Further such delivery systems may not be well accepted in case of pediatric and geriatric preparations where patient compliance is very important.

U.S. Pat. No. 6,001,392 discloses a controlled release syrup suspension for the oral administration containing dextromethorphan, adsorbed on to a polystyrene sulfonate ion exchange resin. The drug polymer complex is coated by a mixture of ethyl cellulose or ethyl cellulose latexes with plasticizers and water dispersible polymers such as SURELEASE™. For the drugs where immediate release is required for rapid action, the controlled release of the active ingredient may not be favored and a delay in release may also be of concern for drugs having a limited absorption window.

The use of ion exchange resin to adsorb drugs containing amino groups for taste masking has found limited applicability in masking the taste of highly bitter drugs and also where the drug is to be dispersed in a liquid oral composition for long duration of time.

Complexation is yet another method for taste masking of bitter drugs. U.S. Pat. No. 4,808,411 discloses a taste masked composition comprising 25 to 95% of erythromycin and about 75 to 5% of carbomer where the drug and carbomer are held together by ionic interactions between erythromycin and carbomer. The complex is further coated with a functional polymer, hydroxy propyl methylcellulose phthalate to make preparation palatable. Erythromycin is released slowly from the complex to avoid a significant perception of bitterness in the mouth. It is clear that slow release, not fast release of bitter medicament is achieved as disclosed in the patent. But complexing alone is not sufficient enough to taste mask and coating with functional polymers is required to attain desired palatability and proper selection of complexing agent is vital since drug release should not be compromised.

Coating of drugs is another method but this alone may prove effective only for moderately bitter drugs or in products where coated particles are formulated as aqueous preparations before administration or are formulated in nonaqueous medium.

Patent Application WO 02/092106 discloses a taste-masked composition comprising polycarbophil and a macrolide antibiotic, clarithromycin. The complex is further coated with an acid resistant polymer Eudragit L100 55™, releasing the drug in the intestine. For certain drugs the bioavailability may not be altered by the use of enteric coating where the drug is released in the small intestine, but the drugs with a narrow absorption window restricted to the upper gastric region, the use of enteric coating may alter the bioavailability. European Patent application EP 0409254 discloses an oral particulate preparation with unpleasant taste being masked using ethyl cellulose and a water swelling agent where the active is released rapidly from the said formulation.

U.S. Pat. No. 5,635,200 discloses a taste-masked preparation of bitter drug ranitidine by a lipid coating and dispersion of these coated particles in the nonaqueous media. U.S. Pat. No. 4,865,851 discloses another method for taste masking highly bitter 1 acetoxy ethyl ester of cefuroxime in particulate form being coated with an integral coating of lipid or a mixture of lipids which serves to mask the taste. The taste masking coating using lipids requires that the melting point of the lipid should be sufficiently high to prevent melting in the mouth and should not be so high that active ingredient itself melts or is chemically degraded. Cefuroxime axetil in a substantially amorphous form with maximum bioavailability has a low melting point of about 70° C. and the difference in the melting of the lipid and drug is very marginal. Also the temperature at which the mixture is atomized is higher than the melting of the lipid. Lipid-based microencapsulation requires a highly sophisticated hot melt granulation process for producing fine particles without adversely affecting the drug molecule.

British Patent 2081092 also discloses a lipid coating for the purpose of taste masking. It was however found that wax coating resulted in poor dissolution of the active ingredients in the alimentary tract. Further the patent discloses a technique to overcome this problem by mixing the waxes with a water swellable polymer. Again the use of the water swellable polymer referred to in the patent makes it less appropriate for the liquid orals like suspensions and dry syrup.

U.S. Pat. No. 5,286,489 describes a porous drug polymer matrix formed by admixing a bitter tasting active ingredient and a methyl methacrylate ester copolymer in at least a 1:1 weight ratio of active ingredient to copolymer, effective to mask the taste of the drug. None of the examples described in the patent disclose the effect of these polymers on the release of the drug from the matrix. Yet from the teaching in the art it is anticipated that the drug release is retarded from the matrix described herein.

Patent Application WO 00/56266 discloses the use of a high viscosity swellable polymer carbomer, in combination with film forming polymethacrylates and channelising agents for taste masking of bitter drugs. The addition of the water swellable polymer aids in the fast release of the active ingredient in the gastric media.

In yet another Patent Application WO 00/76479 a taste masking composition, using a combination of two enteric polymers comprising methacrylic acid copolymer and a phthalate polymer is disclosed. The patent discloses the use of the channelising agents, which comprise the water soluble or water swellable materials to aid the release of the active ingredient. The enteric polymers as disclosed in the patent are known to release the active ingredient in the alkaline pH where the polymers are soluble. The release of the active ingredient will be delayed due to the use of the enteric polymers and in case of the medicaments having a narrow absorption window limited to upper gastrointestinal tract. Such system would therefore be of limited use.

Microencapsulation of highly bitter drug cefuroxime axetil for taste masking is disclosed by M. Cuna et. al (M. Cuna, M. L. Lorenzo, J. L. Vila-Jato, D. Torres, M. J. Alonso, Acta Technologiae et Legis Medicamenti. volume VII, N.3, 1996) using different polymeric materials like cellulose acetate trimellitate, HPMCP-50, HPMCP-55 with the final aim to mask the taste and assuring its release in the intestinal cavity. Alonso et al (M. J. Alonso, M. L Lorenzo-Lamosa, M. Cuna, J. L. Vila-Jato and D. Torres, Journal Microencapsulation, 1997, Volume 14, No. 5, 607-616) describe the encapsulation of cefuroxime axetil, a highly bitter drug, in pH sensitive acrylic microspheres in order to formulate a suspension dosage form. The acrylic polymers used were Eudragit E™, Eudragit RL 100™, Eudragit L100-55™. The cationic Polymer Eudragit E™ showed a negative interaction with cefuroxime axetil. The enteric polymer Eudragit L100-55™ showed a favorable release in alkaline pH.

In the above disclosures the release of cefuroxime axetil was studied in the alkaline media. On the contrary Dantzig et al (Anne H. Dantzig, Dale C. Duckworth, Linda B. Tabas, Biochimica et Biophysica Acta 1191,1994,7-13) showed that cefuroxime axetil is hydrolyzed to cefuroxime in the intestinal lumen by the esterases reducing the cefuroxime axetil concentration in the lumen and resulting in reduced absorption, and low bioavailability of Cefuroxime axetil in humans. Cefuroxime axetil already has a low bioavailability of 32-50% and any further reduction in bioavailability due to formulation aspects should be minimized.

The taste masking formulations should be so designed that the bioavailability of the drugs is not compromised and the use of certain polymers like the enteric coatings should not affect the time to peak. Further the drug should be sufficiently absorbed to ensure effective therapeutic concentration in the plasma. Vogelman et al (B. Vogelman, William A. Craig 108 (5,pt2) 835-40, Journal Pediatric 1986 & B. Vogelman, William A. Craig, S. Ebert, S. Gudmundsson, J. Leggett, J. Infect. Diseases 1988,158(4), 831-47) have established that bactericidal killing is rapid, intensive and increases proportionately to the concentration. In the presence of high concentration of the drug, the killing is complete and almost instantaneous. In some drugs rapid and complete absorption and high systemic concentration are important to elicit the desired therapeutic effect.

Extremely unpleasant tasting active ingredients may require a higher concentration of polymer to obtain the desirable level of taste masking. However this may delay the release of the active ingredient from the formulation. For certain polymers like polymethacrylates the recommended safe daily dose is 2 mg/kg of body weight (Rohm Pharma GmbH. Technical Literature, Eudragit 1990 and Hand book of Pharmaceutical Excipients published by American Pharmaceutical Association & The Pharmaceutical Society of Great Britain) there by restricting the use of higher quantities of the polymer in real life formulation to be administered to humans.

U.S. Pat. No. 5,599,556 disclose liquid formulations where the active ingredient is coated with single outer polymeric coating derived from prolamine cereal grain proteins and plasticizing agent. The bitter drug clarithromycin comixed with polyvinyl pyrrolidone is coated by prolamine to achieve taste masking and the coated particulate matter is dispersed in a suspending medium of pH greater than 6. The coatings are designed to rapidly degrade once the composition leaves mouth and reaches the stomach. Most of the pharmaceutical liquid oral compositions are formulated at a pH of 3.5-5.5 (US Pharmacopoeia/National Formulary 23/NF 18,1995). Some drugs may not be stable at the higher pH and some drugs may not be stable in extreme acidic pH and would tend to degrade over prolonged exposure.

U.S. Pat. No. 5,489,436 discloses chewable tablets made from a coated medicament where the coating is designed to be soluble at the lower pH of the stomach but relatively water insoluble at the higher pH of the mouth. The coatings comprise a polymer blend of dimethylaminoethyl methacrylate and neutral methacrylic acid ester and a cellulose ester. The above mentioned "reverse enteric" coating method of taste masking oral formulation is disclosed in connection with chewable tablets.

Patent Application WO 02/096392 discloses taste masking of highly water soluble drug cetrizine hydrochloride. The polymers like hydroxy propyl methyl cellulose, polyvinyl pyrrolidone, ethyl cellulose are used which effectively mask the taste of cetrizine in tablet form and release the drug immediately under the acidic conditions prevalent in stomach.

It is evident from the above disclosures, that taste masking can be achieved by various methods. The enteric polymers like eudragit L are used for taste masking but the pH of saliva is near 5.8 and these polymers solubilize at pH beyond 5.5. Thus there is a possibility of drug being partially leached. Therefore there is a need for the development of a taste masking polymer such that the bitter taste is completely masked by the polymer at the pH of saliva in mouth and in the reconstitution medium as in case of the liquid orals and further is able to protect the drug in a biologically active form, and also from the moisture in the dosage form preventing it from converting to a solvated or other polymorphic form.

The therapeutic effectiveness of a drug depends upon the ability of the dosage form to deliver the medicament to its site of action at a rate and amount sufficient to elicit the desired pharmacological response. This attribute is referred to as bioavailability. The physicochemical properties of most drugs have greatest influence on the absorption characteristics from the gastrointestinal tract. An important prerequisite for the absorption of a drug by any mechanism is that it must be present in aqueous solution. The poor bioavailability of a drug is a result of its poor aqueous solubility and slow dissolution rate in the biological fluids and poor stability of dissolved drug in the physiological fluids.

Often a chemical substance exists in different ordered states. This is referred to as polymorphism. The polymorphic form, in which the drug is present, can likewise be influenced by the processing techniques. The various crystallographic forms also include pseudo polymorphic forms. It is well known that differences due to polymorphism and pseudo polymorphism observed in certain pharmaceuticals are critical because physical and chemical properties of different crystalline forms of these pharmaceuticals vary. Pharmaceutical drugs and excipients can crystallize in more than one crystallographic form (polymorph, crystalline modifications). Although polymorphs of a substance share the same chemical formula, difference in crystalline structure can affect the physiochemical parameters of the substance such as, solubility, dissolution rate, density (Haleblain, J. K. and Mc Crone, W, Journal of Pharmaceutical Sciences, 58, (8) August, 911-929, (1969) which in turn can affect their important pharmaceutical properties such as bioavailability, stability of drug as well as formulation technology of dosage form. (Byrn, S., Pfeiffer, R., Ganey, M., Hoiberg, C., Poochikian, G., Pharmaceutical Research, 12 (7),945-954, (1995) The physically more stable polymorphic form has lowest energy state, highest melting point and least aqueous solubility. The other forms are the metastable forms, which have higher energy, low melting point and greater solubility. Since the metastable forms have greater solubility and hence greater bioavailability, they are preferred in the formulation. Drugs present in the amorphous forms have higher energy and greater aqueous solubility. The amorphous form of novobiocin has 10 times greater solubility than the crystalline form. Thus the order of dissolution of the different forms of the solid forms of drug is amorphous>metastable>crystalline.

In general, drugs, which are slightly soluble in water and have high crystallinity, have low bioavailability since they have low solubility and low dissolution rate in the gastrointestinal tract. It is well known that converting a crystalline compound into its amorphous state will substantially increase the aqueous solubility of the compound, thereby increasing its bioavailability.

When the process of in vivo drug release is slower than the process of absorption, absorption is said to be dissolution rate-limited. Since dissolution precedes absorption in the overall process, any change in the drug release or dissolution process will subsequently influence drug absorption. See for example Lieberman et al. (1989), Pharmaceutical Dosage Forms: Tablets, Vol. 1, p 34-36 Marcel Dekker, New York. It is clear, therefore, that dissolution time of a composition is one of the important fundamental characteristics for consideration when evaluating compositions intended for fast-onset delivery, particularly where drug absorption is dissolution rate-limited.

Crystalline solids, due to their highly organized, lattice-like structures typically require a significant amount of energy for dissolution. The energy required for a drug molecule to escape from a crystal, for example, is greater than is required for the same drug molecule to escape from a non-crystalline, amorphous form. As a method for obtaining amorphous substances, grinding or forming a solid dispersion is considered. In order to improve their absorbability, several methods for finely grinding drug crystals or for transforming them into amorphous substances have been examined.

Technologies have been developed to overcome the crystallization of the amorphous drugs. Simple strategies for the improvement of drug formulation like increasing the solubility of drugs and thus increasing the fraction of the dose absorbed. The techniques utilized commonly are simple barrier methods including coating and encapsulation some of them include use of the chemical carriers to increase gastrointestinal absorption for the oral delivery of such difficult to formulate molecules.

U.S. Pat. No. 4,673,564 discloses the method for the preparation of sustained release pharmaceutical composition of amorphous nicardipine obtained by friction-pulverizing crystalline nicardipine or its salt in presence of the polymer, hydroxypropylmethyl cellulose. The pulverization of crystalline nicardipine to a fine powder carried out in a ball mill or a vibrating ball mill for a period of at least 10 to 16 hours. However, the method of forming the dispersion is by, extensive and time-consuming ball-milling, and application of such methods for certain sensitive active ingredients would be limited. Patent Application WO 02/087588 discloses a composition of an amorphous cefditoren pivoxil with excellent stability and release. Amorphous cefditoren pivoxil composition is obtained by pulverizing crystalline cefditoren pivoxil in presence of a pharmaceutically acceptable organic polymer.

By fine-grinding, however, particle diameters become irregular between lots, or inter-particle force is enhanced to cause agglomeration. Drug crystals, which can become amorphous by grinding, are limited.

Other methods reported for the preparation of amorphous drug composition of a pharmaceutically active agent which is normally crystalline and sparingly water-soluble at ambient temperature and pressure, involves the dissolution or dispersion of the drug in the molten solution of a pharmaceutically acceptable vehicle and addition of a stabilization agent to retain the active ingredient in the substantially amorphous form.

In some cases it is possible to melt the crystalline active agent, holding it in the molten state for a finite time and then allow it to cool to an amorphous solid.

U.S. Pat. No. 6,171,599 discloses a method of preparation of amorphous efonidipine composition by treating efonidipine hydrochloride, hydroxy propyl methyl cellulose acetate succinate, to a cycle of heating from 85 to 160° C. followed by dipping treatment into a water-containing solution. U.S. Patent Application 20020127 relates to methods and formulations for improving the aqueous solubility of crystalline pharmaceutical compounds having low water solubility by converting them to an amorphous state that is stabilized in a granular pharmaceutical formulation. It discloses a method of improving the aqueous solubility and bioavailability of itraconazole by converting it to the amorphous state, stabilizing this state, and granulating it to form a stabilized granule. The process involves dissolving the active ingredient in the molten solution of hydrophobic vehicle.

In yet another composition of the antifungal drug intraconazole, as disclosed in U.S. Pat. No. 6,497,905, crystalline intraconazole is converted in to amorphous form by dissolving it in molten solution of glyceryl monostearate followed by addition of hydroxy propyl methyl cellulose as stabilizer and further the addition of a disintegrant and formation of the granules with gradual cooling below 5° C. or rapidly cooling the granules to the said temperature.

European Patent Application EP 0852140 discloses a method for converting a sparingly water-soluble medical substance to amorphous state which comprises mixing these components of a sparingly water-soluble medical substance, an amorphous state-inducing agent and an amorphous state-stabilizing agent, and subjecting resulting mixture to heat treatment or mechano-chemical treatment. European Patent Application EP 0462066 relates to a new physical form of gemfibrozil in solid dispersion made of polyvinyl pyrrolidone by melting gemfibrozil and then mixing with the polymer or by solvent evaporation.

All the methods disclosed above are limited to particular active ingredients, which can produce stable amorphous solids and are not degraded by the heating step. There can be some instances where not only the active agent is decomposed and the carrier is deteriorated but also active ingredient is not converted to the amorphous state sufficiently. Further, it has been known that solubility and absorbability of a slightly water-soluble compound are improved by dispersing it in a polymer to form a solid dispersion.

U.S. Pat. No. 5,445,830 discloses a highly absorbable pharmaceutical composition containing methyl 3-phenyl-2 (E)-propenyl 1,4-dihydro-2,6-dimethyl-4-(3-nitrophenyl) pyridine-3,5-dicarboxylate in an amorphous state and a pH-sensitive copolymer of methacrylic acid or its derivatives. The inventors have disclosed that the improved solubility was achieved only if, the compound was maintained in the amorphous state, using pH-sensitive copolymers of methacrylic acid and its derivatives. Further the inventors have disclosed that using polymers such as a cellulose-type high molecular compound or polyvinylpyrrolidone or the like, the solubility of the compound was not improved. The patent discloses the blend of hydrophilic and eudragit polymers in high amount to overcome the said problem. But use of hydrophilic polymers along with the pH sensitive polymer, make such delivery system of little use in application where taste masking of an active in its amorphous form is desired where the drug particles are suspended in aqueous vehicle.

U.S. Patent Application 2002040051, discloses a solid dispersion of ipriflavone in a highly water soluble polymer. The crystalline ipriflavone is converted to an amorphous form during spray drying and the bioavailability is increased. European Patent Application EP 0838218 discloses the controlled release pharmaceutical composition containing a co precipitate of polyvinyl pyrrolidone (PVP) and nifedipine in amorphous form obtained by spray drying the solution comprising of nifedipine and PVP and releasing the drug from the co precipitate over a period of 8-24 hrs.

These compositions are better suited for the sustained release system. Besides the influence of molecular weight on the transformation of the crystalline form as well as bioavailability has not been discussed.

U.S. Pat. No. 6,503,927, discloses a stable amorphous paroxetine hydrochloride composition prepared by employing an aqueous solvent medium containing an acidulant and poly vinyl pyrrolidone and drying the resulting solid dispersion. Yet another U.S. Pat. No. 6,168,805 discloses a process for preparing solid, amorphous composition comprising polyvinyl pyrrolidone. A method for obtaining amorphous paroxetine mixing paroxetine free base with water and polyvinylpyrrolidone having an average molecular weight of from about 10,000 to about 450,000; and drying to form a composition comprising amorphous paroxetine and polymer is disclosed. Poly vinyl pyrrolidone is preferred as the polymer since it does not control or delay the release of said paroxetine from a solid tablet formulation.

The compositions disclosed above making use of poly vinyl pyrrolidone are useful in delivering the active ingredients when in contact with the aqueous media but such systems cannot be formulated in the liquid dosage forms since there is a possibility of release of the active in the reconstitution media and also the recrystallization of the active ingredient in contact with the aqueous media.

Patent Application WO 00/71098 discloses the method of preparing a pharmaceutical composition comprising of amorphous paroxetine and maintain it in the amorphous form by the use of a cosolvent polyethylene glycol and a complexing agent crosspovidone. In the above invention use of the cosolvent is essential to maintain the amorphous form of paroxetine and its absence causes the recrystallization of the active ingredient even in the presence of complexing agent. Additives like polyethylene glycol, as a cosolvent will not be useful in pharmaceutical preparation where leaching of drug in aqueous media is not desired.

U.S. Pat. No. 4,857,336 discloses an osmotic delivery system for carbamazepine where the outer wall made of cellulose acetate is permeable to water but impermeable to the components of the core made up of hydroxy propyl methyl cellulose as protective colloid which inhibits the crystal growth of carbamazepine hydrate and a copolymer of vinyl pyrrolidone and vinyl acetate having a molecular weight of 60,000-15,000 as swellable hydrophilic polymer.

U.S. Pat. No. 5,980,942 discloses the drug delivery system comprising a polymer matrix made of a hydrophilic polymer Hydroxy propyl methyl cellulose, hydrophobic polymer ethyl cellulose and crystalline carbamazepine, incorporated into the polymer matrix wherein the polymer converts the carbamazepine into an amorphous anhydrous form. Further the polymer matrix inhibits the transformation of anhydrous carbamazepine into crystallized dihydrate form releasing the amorphous carbamazepine more readily at steady zero-order rate. Such polymeric matrices as mentioned in the patent are more suitable for the modified delivery. Besides these polymers do not exhibit pH dependant solubility characteristic and hence are not suitable for immediate release.

Patent Application WO 03/024426 reveals a controlled release composition comprising carvedilol where carvedilol is converted from crystalline to amorphous form during formulation of solid dispersion and also stabilized. The polymer polyethylene glycol or polyethylene oxide having a molecular weight of about 20,000 are employed in the formulation for this purpose and release drug in a controlled manner from formulation. The stabilizing agent prevents the re crystallization in the composition and increases the shelf life.

U.S. Patent Application 2002006951 discloses an orally deliverable pharmaceutical composition comprising a poorly soluble drug, celecoxib and its composite with the polymer, which has a turbidity-decreasing characteristic, poly vinyl pyrrolidone and cellulosic polymer, hydroxy propyl methylcellulose. According to the disclosure of the patent, the polymers inhibit crystallization and/or precipitation of the drug in simulated gastric fluid and on ingestion. Polymers used in this disclosure comprise HPMC having molecular weight of 150,000 and povidones having a molecular weight of 50,000. This patent discloses inhibition of recrystallization of the drug on exposure to the aqueous media in gastric tract where the drug is exposed to aqueous media for limited period of time. Also in the liquid oral preparations the aqueous medium surrounds the drug during prolonged reconstitution period.

European Patent Application 1027886 discloses a composition comprising a solid dispersion of a poorly soluble drug and stabilizing polymer. The patent discloses that the polymer having glass transition temperature of at least 100° C. measured at 50% relative humidity contributes to retain major portion of the drug in amorphous form. The term "a major portion" of the drug as disclosed herein means that at least 60% of the drug once dispersed in the dispersion is in the amorphous form, rather than the crystalline form. Amorphous drugs present in the dispersion have a tendency to recrystallize over time, and for drugs whose bioavailability is adversely affected if in crystalline form, even 20-30% drug in crystalline form would not be desired.

Cefuroxime axetil is a cephalosporin antibiotic having a high activity against a wide spectrum of Gram-positive and Gram-negative microorganisms. Antibiotics for oral administration should be in a form, which provides high bioavailability, whereby absorption into the bloodstream from the gastro-intestinal tract is maximized. For cefuroxime axetil, the prior art discloses a number of difficulties in making compositions for oral administration providing high bioavailability. Pure cefuroxime axetil can be produced in crystalline form or amorphous form. It can exist in three polymorphic forms: a crystalline form having a high melting point of about 180° C., a substantially amorphous form having a high melting point of about 135° C. and a substantially amorphous form having a low melting point of about 70° C. The crystalline form of cefuroxime axetil, which is slightly soluble in water and forms a gel upon contact with an aqueous medium, is not readily absorbable in the gastro-intestinal tract, rendering its bioavailability on oral administration very low.

Patent Application WO 99/08683 discloses a method for preparing a co precipitate of cefuroxime axetil and a water-soluble excipient like povidone. Cefuroxime axetil used in the formulation is in pure amorphous form. U.S. Pat. No. 6,107,290 discloses the thermal analysis conducted on co-precipitate. PCT application WO 99/08683 shows that a shift in the absorption peak temperature under moist condition reverts to the original position under a dry condition and the water adsorbed on the co-precipitate is judged to be bound water, which causes a physicochemical change in properties of the drug. Further, despite the use of a water-soluble excipient, the dissolution of cefuroxime axetil from the co-precipitate is not facilitated significantly and accordingly, the bioavailability of cefuroxime axetil contained in the co-precipitate is relatively low.

U.S. Pat. No. 6,107,290 discloses a non-crystalline cefuroxime axetil solid dispersant comprising silicon dioxide, water-insoluble additive like microcrystalline cellulose, cross-linked povidone, cross-linked sodium carboxymethylcellulose or a mixture thereof obtained by spray drying. Methods disclosed in this patent may be useful for solid oral dosage forms but may not be applicable for liquid oral preparation where the bitter taste may not be masked.

European Patent Application EP 1077067 discloses a solid composition of cefuroxime axetil being stabilized by zinc salt and cefuroxime axetil obtained in the pure amorphous form by spray drying. Such formulation is best suited for the solid oral dosage form.

U.S. Pat. No. 4,820,833 discloses a method of producing a substantially amorphous form of cefuroxime axetil, which is stable and provides a high level of bioavailability. The patent does not disclose methods to overcome bitter taste of the drug. U.S. Pat. No. 5,847,118 discloses a method for producing amorphous cefuroxime axetil by dissolving crystalline cefuroxime axetil in a highly polar solvent and then adding this to large quantities of water. The patent does not disclose the formulation and stability of the amorphous cefuroxime axetil therein.

U.S. Pat. No. 6,060,599 discloses a method of preparing an amorphous form of cefuroxime axetil by milling it in the presence of the pharmaceutical excipients like sodium lauryl sulfate, colloidal silicon dioxide and starch. In yet another U.S. Pat. No. 6,346,530, a method of preparing a bioavailable composition of cefuroxime axetil is disclosed which contains about 7-25% of crystalline cefuroxime axetil along with the amorphous form with the tablet exhibiting same bioavailability as the pure amorphous form.

Patent application WO 98/43980 discloses the preparation of amorphous cefuroxime axetil by dissolving crystalline cefuroxime axetil in dimethyl sulfoxide and freezing the mixture and later adding water at 5° C. The precipitate obtained is dried in vacuum. Patent Application WO 99/32124 discloses a pharmaceutical composition comprising amorphous 'S' cefuroxime axetil free from the 'R' form. Such compositions as disclosed in the patent application are claimed to be more palatable than the 1:1 racemic mixture.

Patent Application WO 99/44614 discloses a pharmaceutical composition of cefuroxime axetil and silicon dioxide or its hydrate as a micro environmental pH adjuster and as an anti gelling agent for cefuroxime axetil. Silicon dioxide acts as microenvironment pH adjuster avoiding gelling of cefuroxime axetil in the tablet core due to absorption of moisture from air and also due to the penetration of gastric fluid thereby improving the bioavailability.

Patent application WO 02/43707 discloses a taste masking tablet composition of cefuroxime axetil with a double layer film coat where the first coat serves to mask the bitter taste and the second coat delays the rupture time of the tablet beyond 40 seconds.

All the above disclosures have demonstrated the methods of obtaining an amorphous form of drugs such as cefuroxime axetil or methods to improve its bioavailability and taste masking for solid dosage forms. None of the disclosures reveal taste masking of cefuroxime axetil in a liquid oral preparation and polymers for retaining it in the amorphous form and releasing the same immediately in the stomach without compromising the bioavailability.

Our co-pending patent application No NF 403/2003 discloses and claims taste masked compositions of bitter drugs using a new polymer described and claimed in our another co-pending application No. NF 402/2003.

From the prior art it is well understood that the use of polymers along with the crystalline form of drug can convert the same drug into the amorphous form and can also be stabilized by use of polymers or co-solvent for the prevention of re-crystallization. Many of the known water soluble and swellable polymers were employed earlier for the crystallization inhibition and to improve the solubility and dissolution of poorly soluble drugs from the pharmaceutical compositions. Such polymeric systems would be of little application in taste masking of the drug in solid as well as liquid compositions.

Therefore there remains a need in the art for a means to inhibit crystallization of a drug existing in polymorphic form, in reconstitution media for liquid orals comprising of a poorly water-soluble drug, and in particular for such drugs which have a tendency to undergo polymorphic transformation in presence of the solvents.

OBJECTS OF THE INVENTION

The main object of the present invention is to achieve taste masking of highly bitter drugs and maintain the active ingredient in the pharmaceutical composition in a substantial amorphous form, such that the bioavailability of the said drug is maintained.

Another object of the invention is to provide a taste masked composition of bitter drugs using a pH sensitive polymer with high molecular weight to inhibit crystallization of the drug existing in a polymorphic form during formulation and at much lower polymer loading.

A further object of the present invention is to provide a taste masked composition using a pH sensitive polymer, which inhibits the release of the active agent in the aqueous media at range of >3.5 such that the leaching of bitter drug in the saliva and also in the reconstitution media, in case of liquid orals is inhibited.

The present invention also discloses effect of polymer molecular weight on inhibition of crystallization tendency of the active ingredient, which leads to enhanced bioavailability.

Yet another object of the present invention is to provide a taste masked bitter drug composition using a pH sensitive polymer, which swells or solubilizes in the acidic environment as found in the stomach such that it releases the active agent rapidly in the stomach without affecting its bioavailability.

SUMMARY OF THE INVENTION

Accordingly the present invention provides a taste masked pharmaceutical composition with enhanced bioavailability comprising a pH sensitive polymer of the formula $P[A_{(x)}B_{(y)}C_{(z)}]$: D wherein 'A' is a hydrophobic monomer, 'B' is a basic monomer, 'C' is a hydrophilic monomer and 'D' is a drug existing in polymorphic form, wherein X is in the range of 30 to 95%, Y is in the range of 5 to 70% and Z is in the rang of 0 to 65% all expressed in terms of weight and ratio of P: D is in the range of 30:1 to 0.2:1

In one embodiment of the present invention the molecular weight of the polymer ranges from 50,000 to 7,00,000.

In another embodiment of the invention, the hydrophobic monomer (A) comprises of derivatives of acrylic and methacrylic acid exemplified by cyclohexyl acrylate, dodecyl acrylate, 2 ethyl hexyl acrylate, octyl acrylate, tertiary butyl acrylate, phenyl acrylate, butyl acrylate, methyl methacrylate, benzyl methacrylate, cyclohexyl methacrylate, phenyl methacrylate, tertiary butyl methacrylate, butyl methacrylate, 2 ethyl hexyl methacrylate, propyl methacrylate, preferably the derivatives of the acrylic and methacrylic acid are exemplified by methyl methacrylate, butyl methacrylate and butyl acrylate, most preferably methyl methacrylate.

In yet another embodiment the basic monomer (B) is a derivative of amino alkyl acrylic acid and methacrylic acid like dimethyl amino ethyl acrylate, diethyl amino ethyl acrylate, dimethyl amino ethyl methacrylate, diethyl amino ethyl methacrylate, piperidine ethyl methacrylate, 2 tert-butyl amino ethyl methacrylate, and dimethyl amino ethyl methacrylate preferably dimethyl amino ethyl methacrylate and diethyl amino ethyl acrylate.

Further, in yet another embodiment the basic monomer (B) is selected from the group consisting of alkenyl pyridines like 2-vinyl pyridine, 3-vinyl pyridine, 4-vinyl pyridine and 5-vinyl 2 picoline, 2-vinyl 4 picoline, 2 isopropenyl pyridine, isopropenyl pyridine, preferably 4-vinyl pyridine.

In still another embodiment the basic monomer (B) is selected from vinyl quinolines, aminoalkyl vinyl ethers, amino ethyl styrenes and allylic amines, preferably allylic amines.

In still another embodiment the hydrophilic monomer (C) in the present invention comprises of derivatives of methacrylic acid like hydroxy ethyl methacrylate, hydroxy propyl methacrylate, hydroxy ethyl ethyl methacrylate, preferably hydroxy ethyl methacrylate and hydroxy ethyl ethyl methacrylate, most preferably hydroxy ethyl methacrylate.

In yet another embodiment the bitter drugs used comprise of macrolide antibiotics exemplified by erythromycin, azithromycin and clarithromycin, fluroquinolones exemplified by ciprofloxacin, enrofloxacin, ofloxacin, gatifloxacin, levofloxacin and norfloxacin, cephalosporins exemplified by cefuroxime, cephalexin, cephadroxil, cepfodoxime proxetil, nonsteoroidal and anti-inflammatory and analgesic drugs such as ibuprofen, diclofenac sodium and COX 2 inhibitors like etoricoxib and celecoxib, antihistamic drugs like chlorpheniramine maleate, oxazolidinones like linezolid and other drugs like dextromethorphan preferably cefuroxime axetil and celecoxib.

In yet another embodiment the polymer to drug ratio for optimal taste masking and inhibition of crystalline transformation of the drug existing in polymorphic form thereby increasing the bioavailability of drug is 30:1 to 0.2:1 by wt preferably 5:1 to 0.4:1 by wt.

The taste masked composition of the present invention can be obtained by coating of the drug using of pH sensitive polymer either by microencapsulation, spray drying, fluid bed processing, co precipitation in a non solvent or by tray drying method. The drug is dispersed within the polymer matrix.

In the embodiment of the present invention the pharmaceutical composition is prepared by co-precipitating the drug polymer solution in a nonsolvent or tray drying the drug polymer solution.

The pharmaceutical composition of the present invention can be formulated as solid dosage form like chewable, effervescent and dispersible tablets and liquid dosage form like dry syrup and suspensions.

In the preferred embodiment of the present invention the taste masked composition can be formulated as suspension or dry syrup.

The present invention provides a pharmaceutical composition comprising a solid dispersion of a bitter tasting drug in a polymorphic form being dispersed in the polymer matrix where the taste masking pH sensitive polymer reduces crystallization tendency of the polymorphic drug.

The pH sensitive polymer used for taste masking essentially comprises of the hydrophobic monomer, hydrophilic monomer and a basic monomer.

The present invention also provides a process for preparing pH sensitive polymer, which comprises bulk or solution polymerization, preferably solution polymerization.

In yet another embodiment of the present invention, the solution polymerization is done in the presence of solvent. The solvent used for polymerisation process can be any solvent in which the monomers are soluble, selected from aromatic hydrocarbons, chlorinated hydrocarbon, alcohols, esters, ketones, formamides, tetrahydrofuran, dioxane and dimethyl sulfoxide, preferably dimethyl formamide wherein the ratio of solvent to monomer is 20 to 100% by wt of monomer, preferably 30 to 80, most preferably 30 to 70% by wt of monomer.

In yet another embodiment of the present invention the solution polymerization is done in the presence of a free radical initiator which is chosen from a family comprising of azocompounds, peroxides, hydroperoxides, peracids and peresters, preferably the azo initiator comprising of azo-bis-cyano valeric acid, azo-bis-diphenyl methane, azo-bis-methyl isobutyrate and azo-bis-isobutyronitrile most preferably azo bis isobutyronitrile wherein the % by weight of initiator to monomer is 0.1 to 5, preferably 0.2 to 3% by weight of monomer.

In yet another embodiment the pharmaceutical composition has a substantial amount of the drug in the amorphous form in the resulting dispersion such that the bioavailability of the drug is not affected. The molecular weight of the pH sensitive polymer and its viscosity is responsible for the inhibition of the crystallization of the drug and to maintain it in substantially in amorphous form. The pH sensitive polymer in the pharmaceutical composition prevents the leaching of the drug in the aqueous media of neutral or near neutral pH from 3.5 to 7 such that the drug release is retarded in the saliva and also in the reconstitution media in case of liquid oral giving a taste masked composition with enhanced palatability and releasing major portion of the drug in the gastric region as immediate release.

In particular, the invention comprises a stable taste-masking composition, which can be formulated into liquid suspension capable of being ingested without producing the unpleasant taste associated with the active agent, while still providing immediate bioavailability upon exposure to the pH levels found in the stomach of a human. The taste masking property of the claimed composition is stable in that such compositions are able to mask the unpleasant taste of the active agent for a substantial period of time when stored as a liquid suspension, i.e., minimal leakage of the active agent from the dispersion occurs during storage and the moisture barrier property of the pH sensitive polymer prevents the crystallization of the amorphous drug molecule in aqueous media.

BRIEF DESCRIPTION OF THE ACCOMPANYING DRAWINGS

FIG. 1 describes the X Ray diffraction pattern for the pharmaceutical composition with lower loading of low molecular weight polymer as disclosed in example 4.

Figure 2:
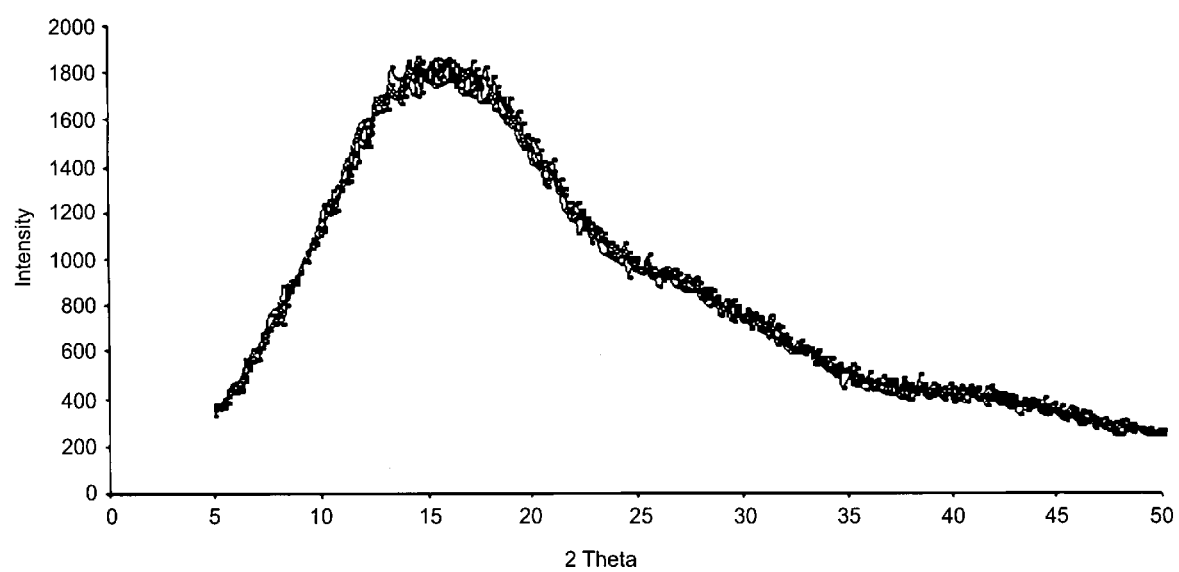

FIG. 2 describes the X Ray diffraction pattern for the pharmaceutical composition with higher loading of low molecular weight polymer as disclosed in example 5.

Figure 3:
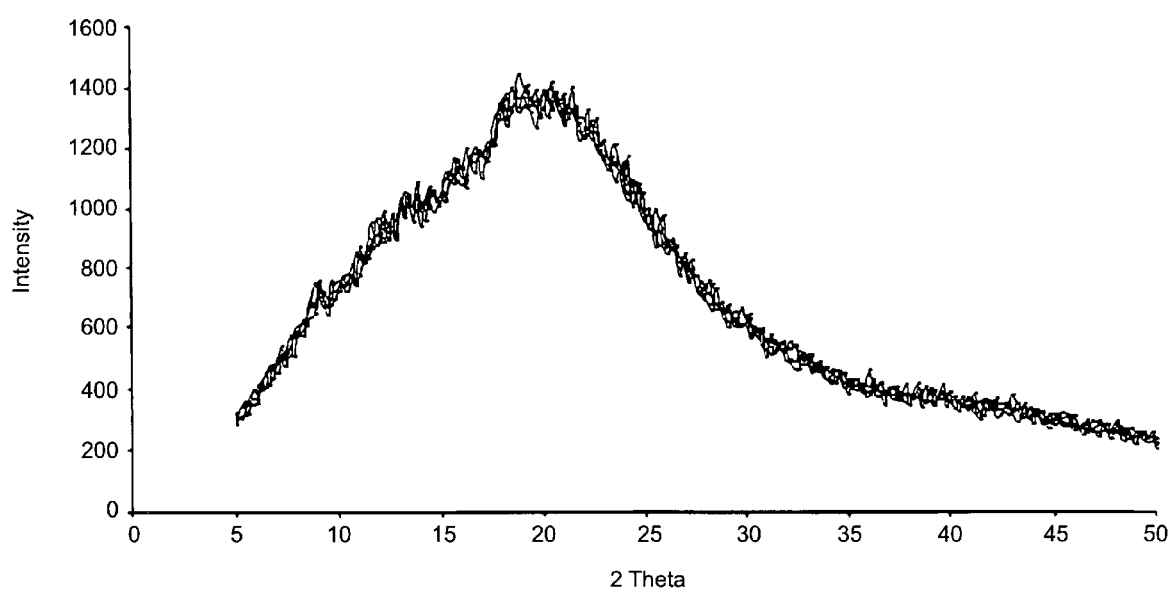

FIG. 3 describes the X Ray diffraction pattern for the pharmaceutical composition with lower loading of high molecular weight polymer as disclosed in example 6.

Figure 4:
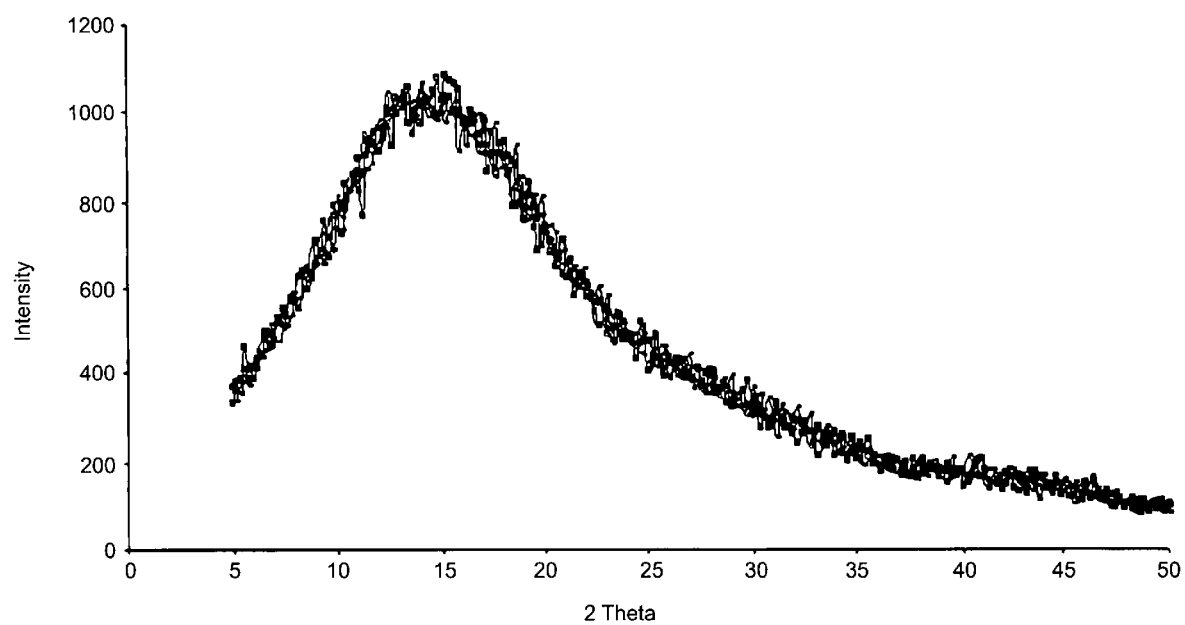

FIG. 4 describes the X Ray diffraction pattern for the pharmaceutical composition with higher loading of high molecular weight polymer as disclosed in example 7.

Figure 5:
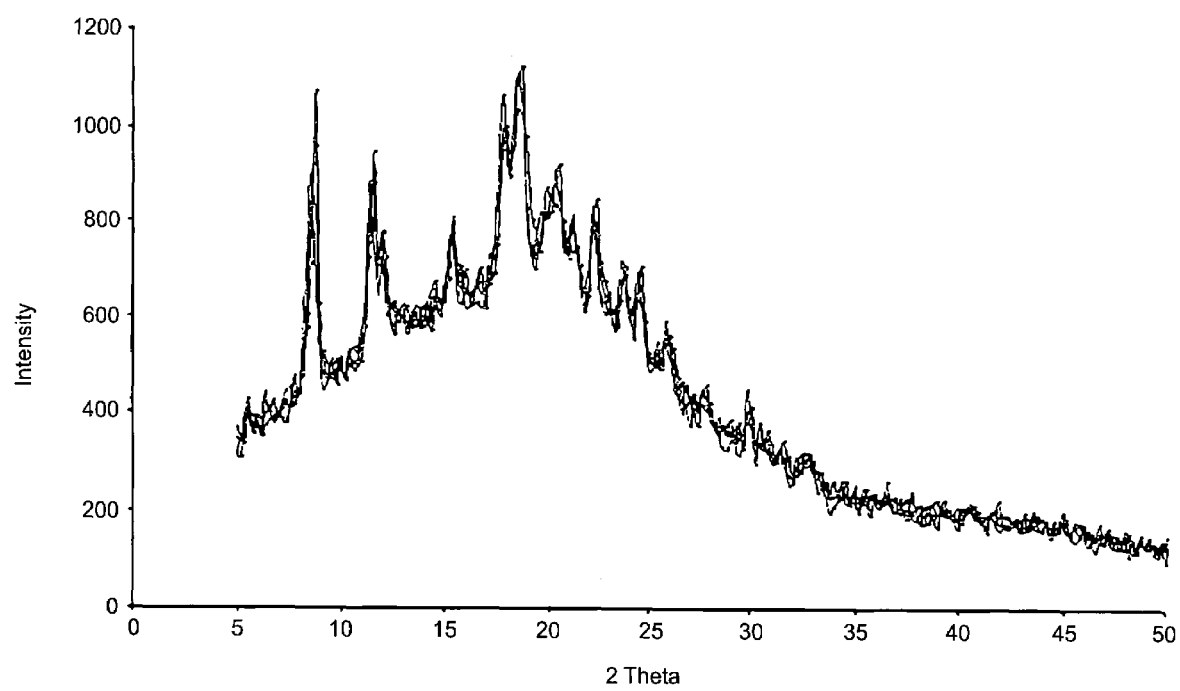

FIG. 5 describes the X Ray diffraction pattern for the pharmaceutical composition with lower loading of low molecular weight polymer as disclosed in example 8.

Figure 6:
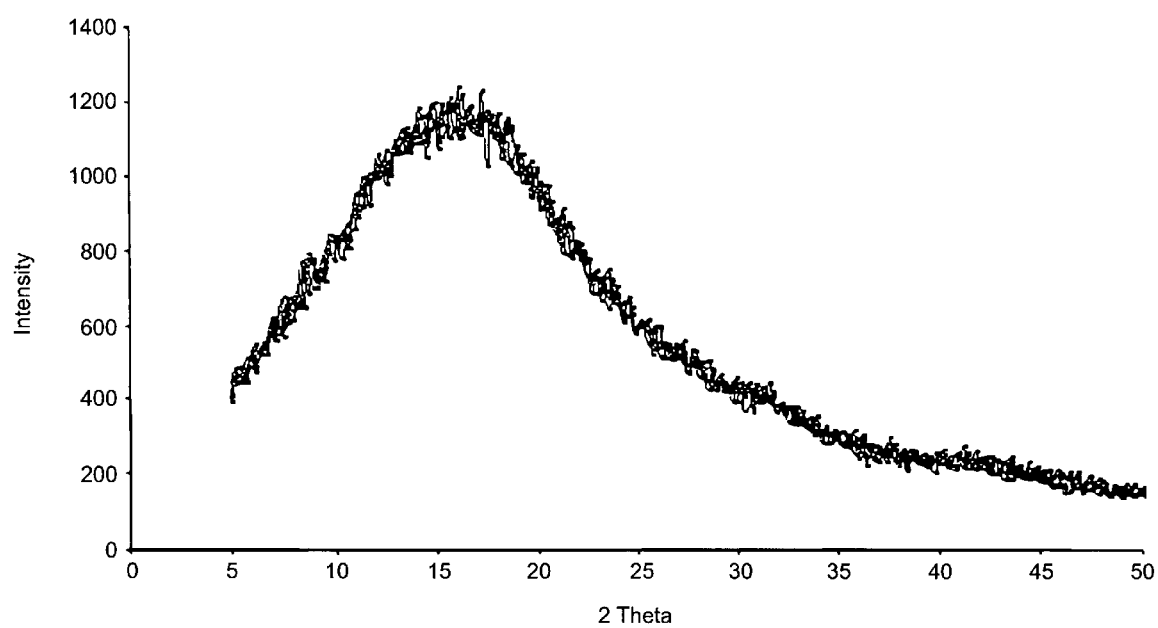

FIG. 6 describes the X Ray diffraction pattern for the pharmaceutical composition with higher loading of low molecular weight polymer as disclosed in example 9.

Figure 7:
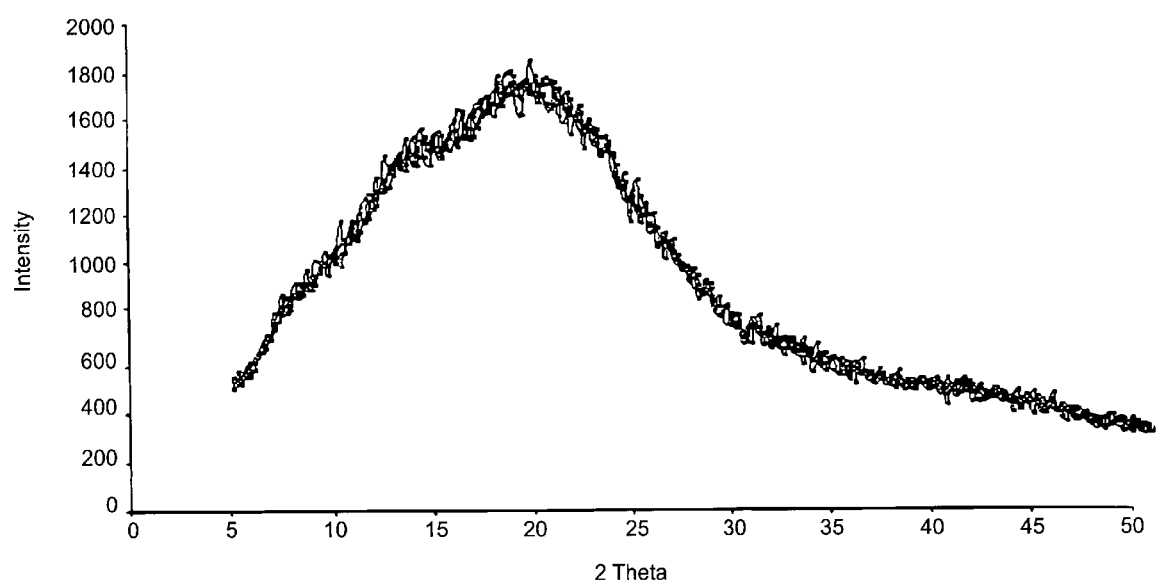

FIG. 7 describes the X Ray diffraction pattern for the pharmaceutical composition with lower loading of high molecular weight polymer as disclosed in example 10.

Figure 8:
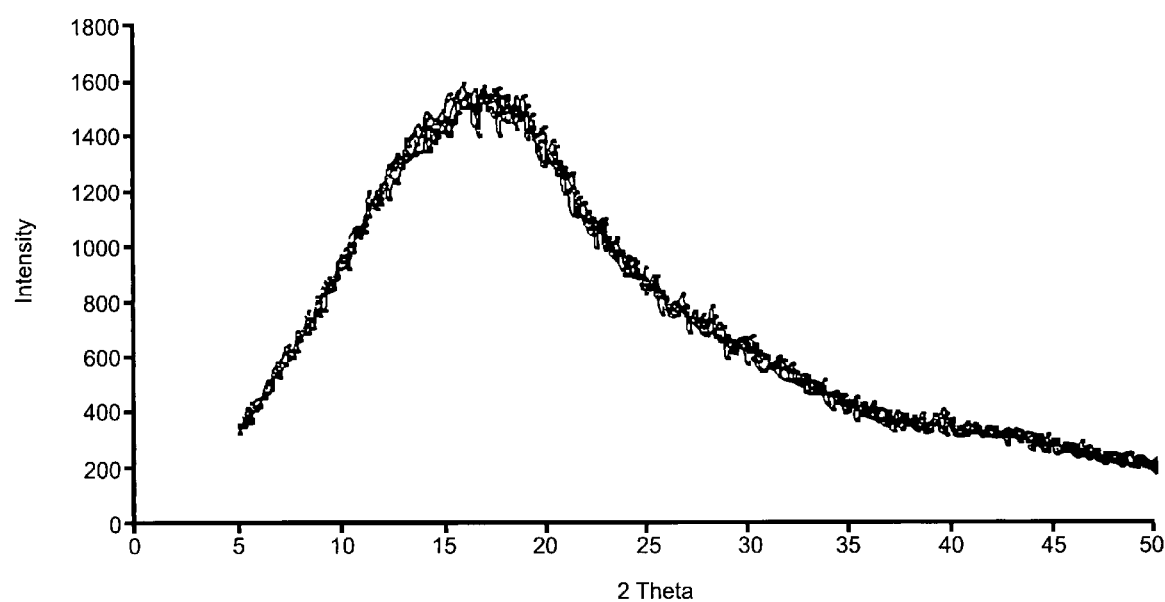

FIG. 8 describes the X Ray diffraction pattern for the pharmaceutical composition with higher loading of high molecular weight polymer as disclosed in example 11.

Figure 9:
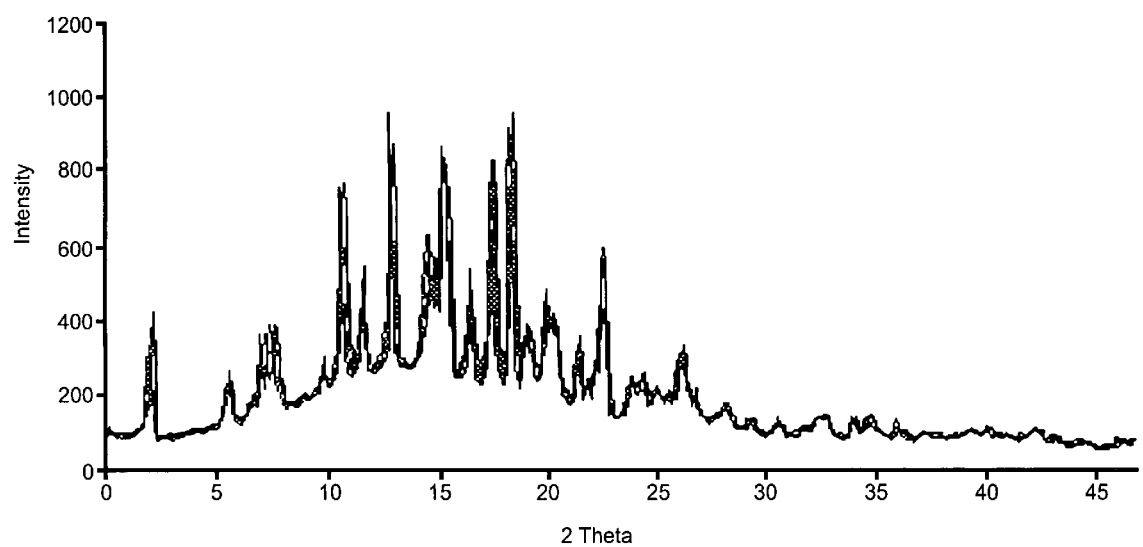

FIG. 9 describes the X Ray diffraction pattern for the pharmaceutical composition with lower loading of low molecular weight polymer as disclosed in example 12.

Figure 10:
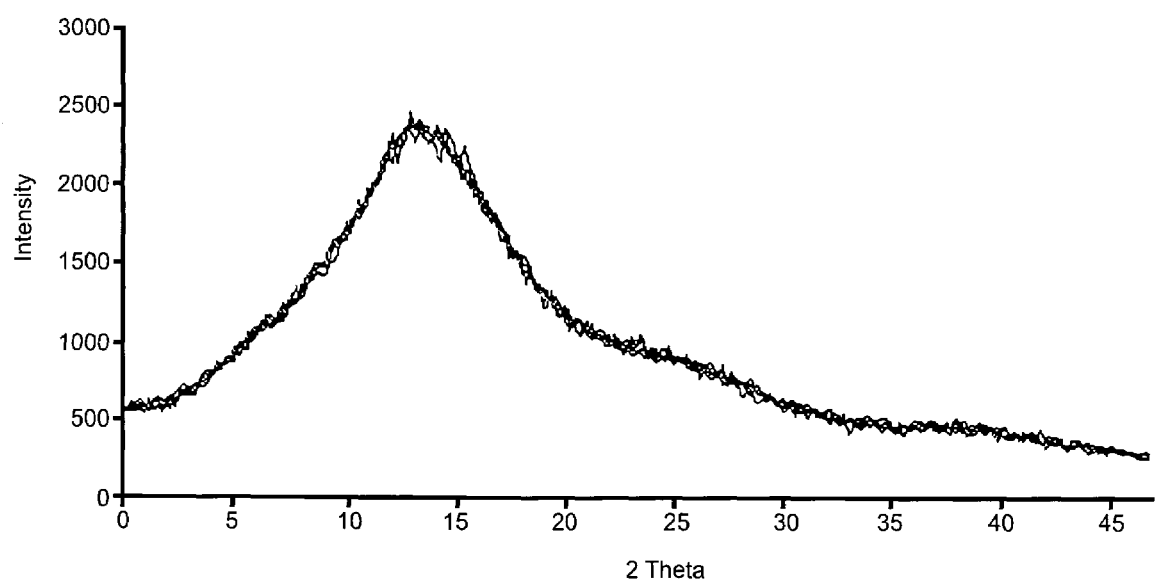

FIG. 10 describes the X Ray diffraction pattern for the pharmaceutical composition with higher loading of low molecular weight polymer as disclosed in example 13.

Figure 11:
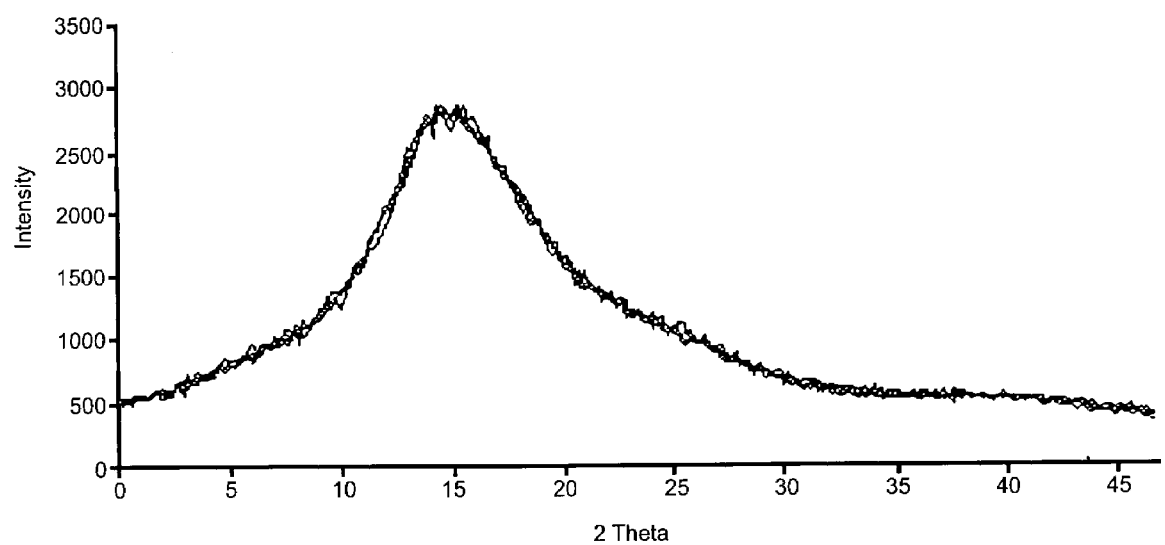

FIG. 11 describes the X Ray diffraction pattern for the pharmaceutical composition with lower loading of high molecular weight polymer as disclosed in example 14.

Figure 12:
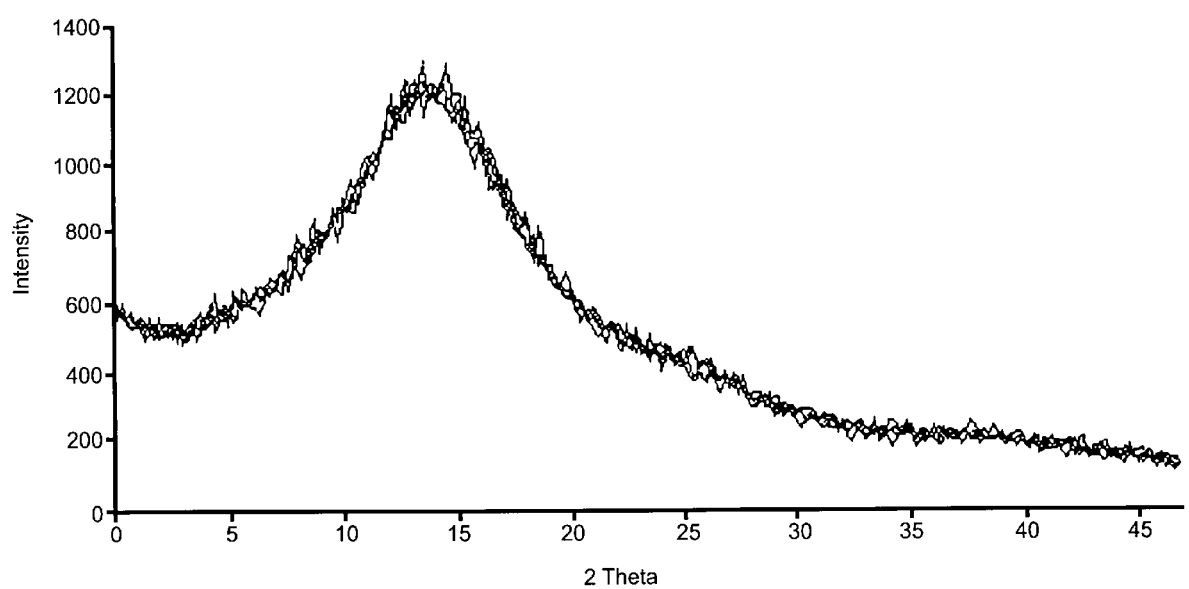

FIG. 12 describes the X Ray diffraction pattern for the pharmaceutical composition with higher loading of high molecular weight polymer as disclosed in example 15.

Figure 13:
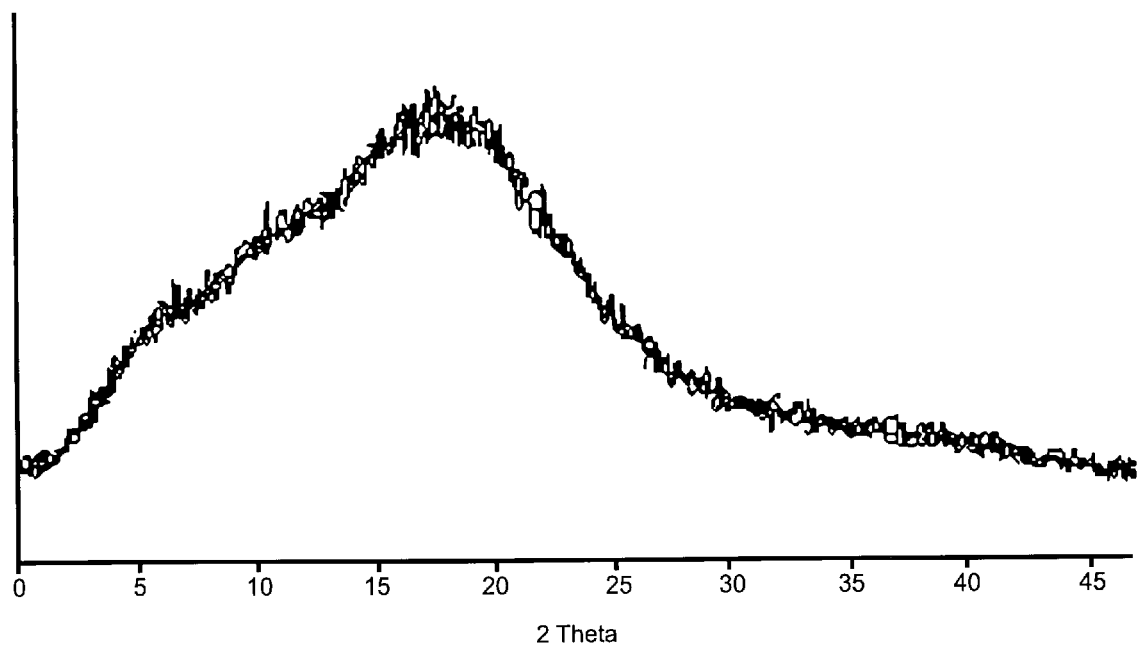

FIG. 13 describes the X Ray diffraction pattern for the pharmaceutical composition with a blend of lower weight polymer and high molecular weight polymer at lower loading as disclosed in example 16.

Figure 14:
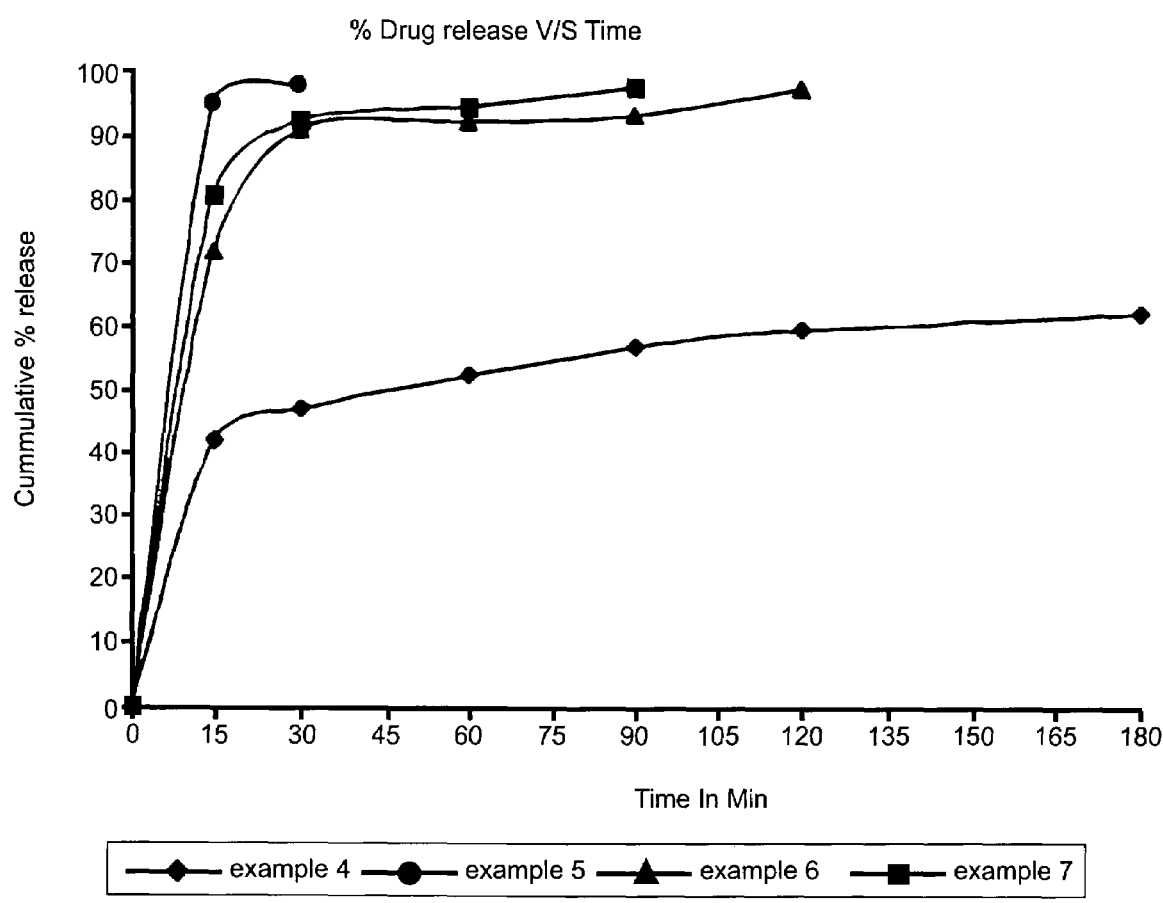
Figure 15:
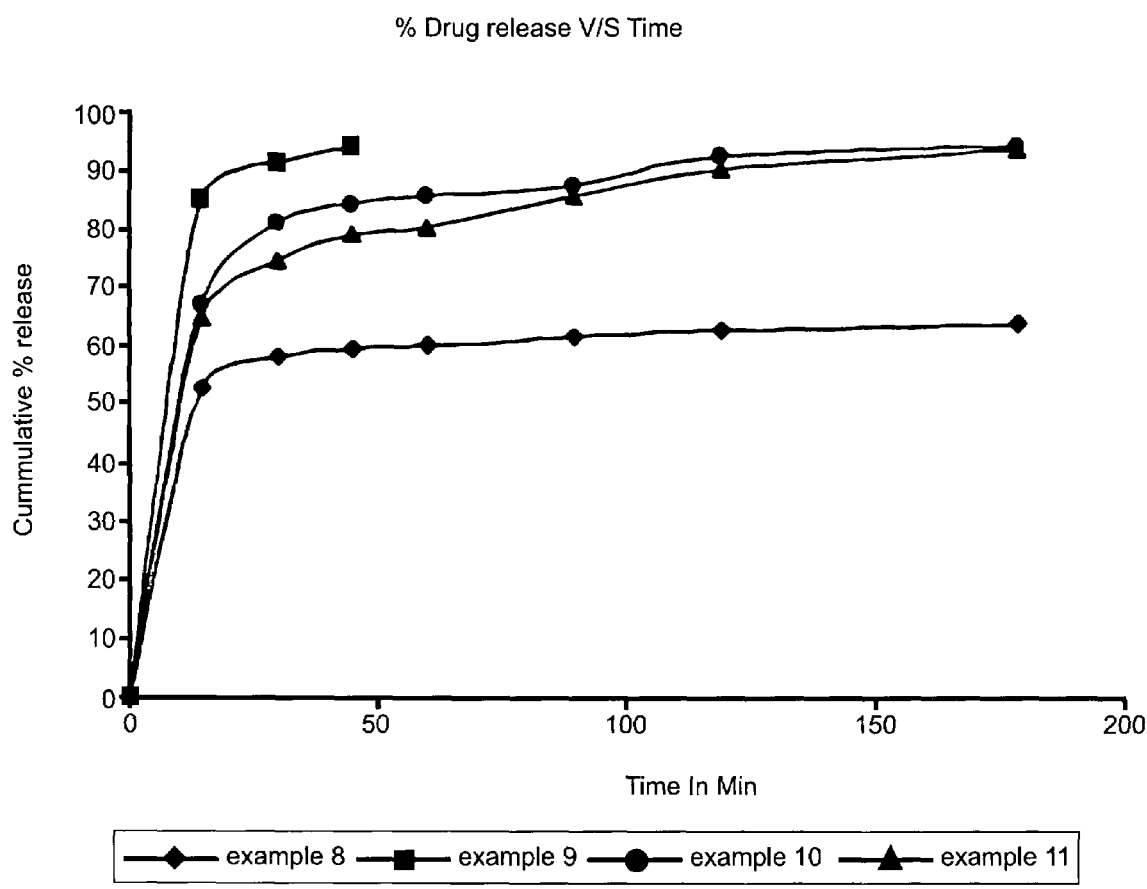

FIGS. 14 & 15 describe release of drug cefuroxime axetil v/s time in 0.07 N HCL buffer.

DETAILED DESCRIPTION OF THE INVENTION

Drug substances, having partial solubility have been found to decrease in crystallinity when mixed with different polymers and excipients. Amorphous form of the drug is often unstable and can revert to the crystalline form. Solid dispersion techniques have been used to stabilize the amorphous forms. The present invention discloses the use of the high molecular weight pH sensitive polymer in a minimum amount, sufficient to form the taste masked solid dispersion and to retain the active ingredient in an amorphous form.

The present invention discloses a pharmaceutical composition comprising a pH sensitive polymer which reduces crystallization tendency for a drug existing in polymorphic form, where the pH sensitive polymer comprises essentially of a hydrophobic monomer in 95 to 30% by weight, a hydrophilic monomer in 10 to 60% by weight, and a basic monomer in 5 to 70% weight in the said polymer, where the molecular weight of the said polymer ranges from 50,000 to 7,00,000 contributing to reduction in crystallization of the drug, wherein the drug is present in a dispersed or coated form within the polymer matrix, such that the drug is in substantially amorphous form and is released immediately in the gastric fluid, at the same time inhibiting drug release at the pH of saliva or the reconstitution pH in case of liquid orals.

The present invention provides a taste-masked composition comprising an active agent coated by a pH sensitive polymer. The pH sensitive polymer of the present invention swells and dissolves in the acidic pH as found in the stomach and releases the drug without causing any delay. The pH sensitive polymer of the present invention remains completely deswelled and is practically insoluble in the pH range >3.5. Since the polymer is insoluble at the pH range >3.5, the leaching of drug in the aqueous medium in which the dry syrups are reconstituted, is inhibited and also the same effect will be exerted in the suspensions. The pH of the saliva is near neutral, so the polymer disclosed in the present invention will retard the drug release and thus provide taste masking. The pH sensitive polymers of the present invention can also be used to taste mask the solid dosage forms which are required as immediate release preparations like the conventional tablets, dispersible tablets and the chewable tablets. The pH sensitive polymer of the present invention is not soluble and does not swell in water so that it can be used in the preparation of the dispersible tablets where the tablet is to be dropped in water before ingestion and is to release the drug almost immediately. Since the polymer swells and solubilizes fast in the acidic media, it further aids in wetting and solubilization of the active ingredient. The pH sensitive polymer may be used to coat and mask the taste of the drug in case of the chewable tablet where the active ingredient is in contact with the taste buds for considerable time.

The polymeric formulations covered in the scope of the present invention are particularly suitable for taste masking drugs, which are extremely bitter in taste, which exhibit varying levels of bioavailability depending upon the polymorphic form in which they exist and when the amorphous form is preferred over others, and which need to be released rapidly in the stomach. The application of the pH sensitive polymer of the present invention is however not restricted to the taste masking of drugs exhibiting polymorphism. Any drug which has an unpleasant and bitter taste can be incorporated in the polymeric coating. Examples of the bitter, unpleasant tasting drugs which may be used include, but are not limited to macrolide antibiotics exemplified by erythromycin, azithromycin and clarithromycin, fluroquinolones exemplified by ciprofloxacin, enrofloxacin, ofloxacin, gatifloxacin, levofloxacin and norfloxacin, cephalosporins exemplified by cefuroxime, cephalexin, cephadroxil, cepfodoxime proxetil, nonsteoroidal and anti-inflammatory and analgesic drugs such as ibuprofen, diclofenac sodium and COX 2 inhibitors like etoricoxib and celecoxib, antihistamic drugs like chlorpheniramine maleate, oxazolidinones like linezolid and other drugs like dextromethorphan. The drug itself or its pharmaceutically acceptable salt or ester may be used in the present invention.

Drug molecules like cefuroxime axetil tend to gel in presence of aqueous media. Also if the tablets are not protected from moisture during storage, they result in poor dissolution and lower bioavailability. So the liquid oral preparation of cefuroxime axetil needs to protect the drug during reconstitution period from aqueous environment. Cefuroxime axetil has a limited absorption region in the gastrointestinal tract as the enzyme esterase hydrolyses it to cefuroxime, which cannot be absorbed across the gastro intestinal tract thereby reducing its bioavailability. Cefuroxime axetil is also associated with an extremely bitter taste. Pharmaceutical compositions of cefuroxime axetil are therefore required to be taste masked. The use of water soluble and enteric coating polymers for Cefuroxime axetil are therefore of limited use.

In the preferred embodiment of the present invention, the solid dispersion comprises of bitter drug cefuroxime axetil, the second-generation cephalosporin antibiotic in its amorphous form. Amorphous Cefuroxime axetil shows a tendency to crystallize in the presence of the solvents, which is suppressed by the pH sensitive polymers disclosed in this invention. The pH sensitive polymers of higher molecular weight synthesized in the present invention are more effective at lower loadings in taste masking and crystallization inhibition of the bitter drug cefuroxime axetil in the solid dispersion and also when reconstituted in an aqueous syrup base of pH 4.5 during the entire reconstitution period. The polymer also inhibits transformation of the amorphous cefuroxime axetil in to the crystalline form during the formulation and also the period of 7 days during which the reconstituted suspension is generally consumed. Cefuroxime axetil is released almost immediately and completely from solid dispersion in gastric region as shown in examples 4-11 and example 16.

Drugs like carbamazepine are better absorbed in anhydrous and amorphous form and the conversion to the crystalline, dihydrate form leads to lower solubility and also lower bioavailability. Further drug molecules like celecoxib have low aqueous solubility and so the amorphous form is preferred for rapid release formulation. Yet the drug shows a tendency to crystallize in presence of gastric medium. Such drugs require a protective polymer coating, which acts as a moisture barrier and prevents the polymorphic transformation of the drug. From the prior art it is evident that varying loadings of diverse polymers have been employed to taste mask bitter drugs and also to convert crystalline drug to amorphous form and retain in the latter form.

The commercially available polymer, Eudragit E from Rohm GmbH, Darmstadt, Germany (a Dimethyl Amino Ethyl Methacrylate copolymer) is useful as a taste-masking agent Generally this polymer is insoluble in the basic pH. However it is found that the polymer shows some degree of swelling, in the neutral to slightly acidic pH causing problem. When Cefuroxime axetil was coated using the Eudragit E polymer it showed a negative interaction with the drug (M. J. Alonso, M. L Lorenzo-Lamosa, M. Cuna, J. L. Vila-Jato and D. Torres, Journal of Microencapsulation, 1997, Volume 14, No. 5, 607-616).

The pH sensitive polymers of the present invention have the advantage that they can bring about taste masking and crystallization inhibition at lower loadings. This helps in lowering the polymer loading in the formulation, will be economically attractive and will also help comply with the regulatory requirements in terms of daily dosage. The pH sensitive polymers having high molecular weight and higher solution viscosity as described in the present invention retain the amorphous drug in the same form and further inhibit conversion of the drug in the crystalline form in the presence of the solvents. Further the polymer does not need any adjuvant like a channelising agent or a water-soluble or water swellable excipient to aid in the release of drug in stomach such that time to peak and also absorption of drug are not delayed as observed in case of the enteric polymers, which delay the release.

The pH sensitive polymer described in the present invention comprises of the hydrophobic monomer polymerized along with a basic monomer or a hydrophobic monomer polymerized along with a hydrophilic monomer and a basic monomer. In the preferred embodiment of the present invention, the pH sensitive polymer, which inhibits the crystallization of the bitter drug capable of existing in various polymorphic forms, comprises essentially of a hydrophobic monomer, a hydrophilic monomer and a basic monomer.

The hydrophobic monomer comprises of derivatives of the acrylic and methacrylic acid exemplified by cyclohexyl acrylate, dodecyl acrylate, 2 ethyl hexyl acrylate, octyl acrylate, tertiary butyl acrylate, phenyl acrylate, butyl acrylate, methyl methacrylate, benzyl methacrylate, cyclohexyl methacrylate, phenyl methacrylate, tertiary butyl methacrylate, butyl methacrylate, 2 ethyl hexyl methacrylate, propyl methacrylate, preferably the derivatives of the acrylic and methacrylic acid are exemplified by methyl methacrylate, butyl methacrylate and butyl acrylate, most preferably methyl methacrylate.

The basic monomer comprises of various derivatives of amino alkyl acrylic acid and methacrylic acid like dimethyl amino ethyl acrylate, diethyl amino ethyl acrylate, dimethyl amino ethyl methacrylate, diethyl amino ethyl methacrylate, piperidine ethyl methacrylate, 2 ter-butyl amino ethyl methacrylate, preferably dimethyl amino ethyl methacrylate and diethyl amino ethyl acrylate.

The basic monomer can also comprise of the group of alkenyl pyridines like 2-vinyl pyridine, 3-vinyl pyridine, 4-vinyl pyridine and 5-vinyl 2 picoline, 2-vinyl 4 picoline, 2 isopropenyl pyridine, iso propenyl pyridine, preferably 4-vinyl pyridine.

The basic monomer (B) is selected from vinyl quinolines, amino alkyl vinyl ethers, amino ethyl styrenes and allylic amines, preferably allylic amines. The hydrophilic monomer in the present invention comprises of derivatives of methacrylic acid like hydroxy ethyl methacrylate, hydroxy propyl methacrylate, hydroxy ethyl ethyl methacrylate, preferably hydroxy ethyl methacrylate and hydroxy ethyl ethyl methacrylate, most preferably hydroxy ethyl methacrylate.

The pharmaceutical composition is capable of releasing the drug rapidly in the stomach of the patient. The pH sensitive taste masking polymer of the present invention is insoluble at pH range >3.5 and does not release the drug at the pH of the saliva and also in the media of pH >3.5. The pH sensitive polymer is further capable of inhibiting crystallization of the drug existing in the polymorphic form during the formulation and retains the drug in the amorphous form.

[A] Preparation of the pH Sensitive Polymer

The pH sensitive polymer synthesized comprises of hydrophobic monomer polymerized along with a hydrophilic monomer and a basic monomer. The pH sensitive polymer can be synthesized by bulk or solution polymerisation. The pH sensitive polymer of the present invention is synthesized by solution polymerisation. The pH sensitive polymer is synthesized by dissolving the hydrophobic, hydrophilic and basic monomer in the presence of a solvent, dimethyl formamide.

Further the pH sensitive polymer of the present invention is polymerized in presence of a free radical initiator. The initiator is dissolved in the solvent along with the hydrophobic, hydrophilic and basic monomer to yield the pH sensitive polymer. The free radical initiator used for the synthesis of the pH sensitive polymer is chosen from a family of azo compounds exemplified by azo-bis-isobutyronitrile.

The pH sensitive polymer is synthesized using hydrophobic monomer methyl methacrylate, hydrophilic monomer hydroxy ethyl methacrylate and basic monomer vinyl pyridine. The monomers were dissolved in the solvent, dimethyl formamide. An azo initiator, azo bis isobutyronitrile was added to the monomer solution in dimethyl formamide. The reaction mixture was purged with the nitrogen gas to provide the inert atmosphere. The polymerization reaction was carried out by heating the reaction mixture to 60-70° C. for a period of 15-18 hours. The polymer so synthesized was recovered by precipitating in a nonsolvent. The nonsolvent like petroleum ether or diethyl ether or water can be used.

The polymer was dried at 27° C. under vacuum. The polymer was characterized for viscosity and molecular weight and for composition.

The polymers used for inhibition of the crystallization of the polymorphic drug at lower polymeric loading are polymers, which have higher molecular weight and higher solution viscosity. The polymers of higher molecular weight were synthesized in the present invention using the fixed monomeric composition and by varying the amount of initiator and the solvent. The polymers of higher molecular weight were also synthesized by reducing the initiator concentration with respect to the monomer content. Alternately the polymers of high molecular weight can be synthesized by reducing the amount of the inert solvent with respect to the monomer content. The molecular weights of the polymers synthesized were determined using Waters gel permeation chromatography and polystyrene standard (Polysciences Inc. USA) as reference using Styragel columns. The intrinsic viscosity for polymer solutions in the range 0.1 to 1% w/w in dimethyl formamide was determined by using the Ubbelohde Viscometer for dilution sequences, Schott Gerate, GmbH. at 30° C. The corresponding intrinsic viscosity values for the molecular weights are shown in the table 1 to 3.

EXAMPLE 1

The pH sensitive polymer is synthesized by solution polymerization. The hydrophobic monomer methyl methacrylate 60% by weight, hydrophilic monomer hydroxy ethyl methacrylate 25% by weight and basic monomer vinyl pyridine 15% by weight were used for the synthesis of the polymer. The monomers were dissolved in the solvent, dimethyl formamide. An azo initiator, azo bis isobutyronitrile was added to the monomer solution in dimethyl formamide. The reaction mixture was purged with the nitrogen gas to provide the inert atmosphere. The polymerization reaction was carried out by heating the reaction mixture to 65° C. for a period of 18 hours. The polymer so synthesized was recovered by precipitating in a nonsolvent. The nonsolvent diethyl ether was used. The polymer was dried at 27° C. under vacuum. The polymer was characterized for viscosity and molecular weight and for composition. The polymer composition, molecular weight and intrinsic viscosity of the polymer are summarized in Table 1.

TABLE 1 pH sensitive polymer for taste masking.

| No | Monomer | Wt % | Initiator[a] | Solvent[a] | Molecular Weight $M_w$ | Intrinsic viscosity dl/g |
|---|---|---|---|---|---|---|
| 1 | Methyl methacrylate | 60 | 0.18 | 68.0 | 58,556 | 0.1596 |
|  | Hydroxyethyl methacrylate | 25 | | | | |
|  | Vinyl Pyridine | 15 | | | | |

[a]% by weight of monomer

EXAMPLE 2 pH sensitive polymers used for inhibition of crystallization of polymorphic drug at lower polymeric loading are polymers, which have higher molecular weight and high viscosity. The polymers of higher molecular weight were synthesized using the hydrophobic monomer, methyl methacrylate 60% by weight, hydrophilic monomer hydroxy ethyl methacrylate 25% by weight and basic monomer vinyl pyridine 15% by weight and varying the amount of initiator and the solvent. The polymers of the higher molecular weight were synthesized by reducing the initiator concentration with respect to the monomer content. Alternately the polymers of high molecular weight could be synthesized by reducing the amount of the inert solvent with respect to the monomer content.

The high molecular weight pH sensitive polymer of the present invention is synthesized by solution polymerization. The hydrophobic monomer methyl methacrylate, hydrophilic monomer hydroxy ethyl methacrylate and basic monomer vinyl pyridine were used for the synthesis of the polymer. The fixed amount of monomers was used for different sets of polymerization reaction. The amount of solvent was gradually decreased for each experiment. The monomers were dissolved in the solvent, dimethyl formamide. An azo initiator, Azo bis isobutyronitrile was added to the monomer solution in dimethyl formamide. The amount of the azo initiator was kept constant with respect to the monomer content in all the sets of the reaction. The reaction mixture was purged with the nitrogen gas to provide the inert atmosphere. The polymerization reaction was carried out by heating the reaction mixture to 65° C. for a period of 18 hours. The polymer so synthesized was recovered by precipitating in a nonsolvent. The nonsolvent used was diethyl ether. The polymer was dried at 27° C. under vacuum. The polymer was characterized for viscosity and molecular weight and for composition. The polymers of different molecular weight synthesized by varying the amount of solvent are shown in table 2.

Alternately, the high molecular weight pH sensitive polymer described in the present invention can be synthesized by solution polymerization varying the amount of the azo initiator. The azo initiator used for polymerization was azobisisobutyronitrile. The hydrophobic monomer methyl methacrylate, hydrophilic monomer hydroxy ethyl methacrylate and basic monomer vinyl pyridine were used for the synthesis of the polymer. A fixed amount of monomers was used for different sets of polymerization reactions. The amount of initiator, azo bis isobutyronitrile was gradually decreased. The amount of the solvent with respect to the monomeric contents was kept constant in all the sets of the reaction. The monomers were dissolved in the solvent, dimethyl formamide. The reaction mixture was purged with nitrogen gas to provide an inert atmosphere. The polymerization reaction was carried out by heating the reaction mixture to 65° C. for a period of 18 hours. The polymer so synthesized was recovered by precipitating in a nonsolvent which was diethyl ether. The polymer was dried at 27° C. under vacuum and characterized for viscosity and molecular weight and for composition. The polymers of different molecular weight synthesized by varying the amount of initiator, azo bis isobutyronitrile are shown in table 2.

TABLE 2

High molecular weight pH sensitive polymer for taste masking obtained by varying the Solvent and Initiator composition.

| No. | Monomer | Wt % | Initiator[a] | Solvent[a] | Molecular Weight $M_w$ | Intrinsic viscosity g/dl |
|---|---|---|---|---|---|---|
| 1 | Methyl methacrylate | 60 | 0.09 | 72.66 | 53,677 | 0.1365 |
|  | Hydroxyethyl methacrylate | 25 | | | | |
|  | Vinyl Pyridine | 15 | | | | |
| 2 | Methyl methacrylate | 60 | 0.09 | 61.46 | 79,743 | 0.3684 |
|  | Hydroxyethyl methacrylate | 25 | | | | |
|  | Vinyl Pyridine | 15 | | | | |

TABLE 2-continued

High molecular weight pH sensitive polymer for taste masking obtained by varying the Solvent and Initiator composition.

| No. | Monomer | Wt % | Initiator[a] | Solvent[a] | Molecular Weight $M_w$ | Intrinsic viscosity g/dl |
|---|---|---|---|---|---|---|
| 3 | Methyl methacrylate | 60 | 0.09 | 34.72 | 2,25,497 | 0.6945 |
|   | Hydroxyethyl methacrylate | 25 | | | | |
|   | Vinyl Pyridine | 15 | | | | |
| 4 | Methyl methacrylate | 60 | 0.09 | 68.03 | 63,189 | 0.3080 |
|   | Hydroxyethyl methacrylate | 25 | | | | |
|   | Vinyl Pyridine | 15 | | | | |
| 5 | Methyl methacrylate | 60 | 0.045 | 68.03 | 1,25,280 | 0.4882 |
|   | Hydroxyethyl methacrylate | 25 | | | | |
|   | Vinyl Pyridine | 15 | | | | |
| 6 | Methyl methacrylate | 60 | 0.0225 | 68.03 | 1,94,344 | 0.5703 |
|   | Hydroxyethyl methacrylate | 25 | | | | |
|   | Vinyl Pyridine | 15 | | | | |

[a]% weight by monomer

EXAMPLE 3

High molecular weight polymers are synthesized using the monomer composition methyl methacrylate 60% w/w, hydroxy ethyl methacrylate 25% w/w and vinyl pyridine 15% w/w in the presence of 51, weight % (of monomer) of dimethyl formamide as solvent and 0.0225% azo bis isobutyronitrile as initiator. The polymerization reaction was carried out by heating the reaction mixture to 60-70° C. for a period of 15-18 hours. The polymer so synthesized was recovered by precipitating in a nonsolvent diethyl ether. The polymer was dried at 27° C. under vacuum. The polymer composition is shown in Table 3.

The high molecular weight polymer is synthesized by using the monomer composition methyl methacrylate 60% w/w, hydroxy ethyl methacrylate 25% w/w, and vinyl pyridine 15% w/w in the presence of 34.72 weight % (of monomer) of dimethyl formamide as solvent and 0.045 weight %(of monomer) of azo bis isobutyronitrile as initiator. The polymerization reaction was carried out by heating the reaction mixture to 60-70° C. for a period of 15-18 hours. The polymer so synthesized was recovered by precipitating in a nonsolvent. The nonsolvent diethyl ether was used. The polymer was dried at 27° C. under vacuum. The high molecular weight polymers are shown in the table 3

TABLE 3

High molecular weight pH sensitive polymers for taste masking obtained by varying the Solvent and Initiator composition.

| S. No. | Monomer | Wt % | Initiator[a] | Solvent[a] | Molecular Weight $M_w$ | Intrinsic viscosity g/dl |
|---|---|---|---|---|---|---|
| 1 | Methyl methacrylate | 60 | 0.0225 | 51.53 | 2,72,177 | 0.9011 |
|   | Hydroxyethyl methacrylate | 25 | | | | |
|   | Vinyl Pyridine | 15 | | | | |
| 2 | Methyl methacrylate | 60 | 0.045 | 34.72 | 3,38,021 | 1.2135 |
|   | Hydroxyethyl methacrylate | 25 | | | | |
|   | Vinyl Pyridine | 15 | | | | |

[a]% weight by monomer

Polymers having a wide range of molecular weight were synthesized and their utility for taste masking and also for the crystallization inhibition was evaluated by formulating the pharmaceutical compositions using a bitter drug, cefuroxime axetil which exists in the polymorphic form and coating the said drug with these pH sensitive polymers.

[B] Preparation of the Pharmaceutical Composition

The pharmaceutical compositions of the present invention can be obtained by coating of the drug using pH sensitive polymer either by microencapsulation, spray drying, fluid bed processing, co-precipitation in a non solvent or by tray drying method. The drug is dispersed within the polymer matrix.

The pharmaceutical composition of the present invention is obtained by tray drying method or alternately by co precipitation of the drug and polymer in a nonsolvent. The polymer is solubilised in a solvent and the drug is solubilised or dispersed in it.

The ratio of the polymer to drug used depends on the molecular weight and viscosity of the polymer such that the polymer is able to inhibit the crystallization of the drug and also retain the taste masking effect. In the embodiment of the present invention the total polymer to drug ratio for optimal taste masking and inhibition of crystalline transformation of the polymorphic drug is 30:1 to 0.2:1 by weight. More preferably the ratio of the polymer to drug is 5:1 to 0.4:1 by weight. In a further preferred embodiment of the present invention the ratio of polymer: drug is 3:1 to 0.6:1 by weight.

The pH sensitive polymer, which masks the taste and reduces crystallization tendency for a drug existing in polymorphic form preferably has a molecular weight in the range of 50,000 to 7,00,000. Further the polymers having a molecular weight 50,000 to 5,00,000 are more preferred. Yet more preferred molecular weight range for the polymer being 1,00,000 to 3,50,000. The most preferred molecular weight range being 2,50,000 to 3,50,000.

Further, the pharmaceutical composition of the present invention can be formulated using the pH sensitive polymer of lower molecular weight, less than 1,50,000 or a polymer of higher molecular weight greater than 1,50,000 to 3,50,000 or a combination of lower molecular weight and higher molecular weight polymer in the ratio 1:1 to 1:5 or 5:1 to 1:1. Preferably the solvent is selected such that the drug and the polymer are both soluble therein. The solvents chosen for the solubilization of the drug and polymer are preferably alcohols like methanol, ethanol, isopropanol, butanol, chlorinated hydrocarbons like dichloromethane, chloroform, ketones like methyl ethyl ketone, methyl iso-butyl ketone and acetone. Preferably the solvents used to dissolve the drug and polymer, are methanol, acetone and dichloromethane. The most preferred solvent to dissolve the drug and polymer being acetone or a mixture of methanol and dichloromethane in the ratio 1:1 to 1:1.5. The solvent used is preferably acetone containing 10 to 0.5% of water by weight.

The taste-masked composition in the form of the solid dispersion can be obtained by co-precipitating the drug and the polymer in the nonsolvent. The process involves dissolving cefuroxime axetil and polymer in acetone containing 0.5-10% water. The resulting mixture is added to petroleum ether maintained at 5° C. The co-precipitate so obtained is dried under vacuum for 24 hrs at room temperature and sized to obtain ASTM mesh 40/60 particles.

An alternate method to obtain taste-masked composition is to either tray dry the drug polymer solution. This involves dissolution of the drug cefuroxime axetil and polymer in acetone containing 0.5-10% water and casting the solution on a tray and drying under vacuum at room temperature and sizing to obtain ASTM mesh 40/60 particles. Taste masked particles and granules obtained may be mixed with flavoring agents such as natural or artificial flavors, citric and tartaric acids, sweeteners such as sucrose, saccharin and aspartame, and other pharmaceutically acceptable excipients to be formulated as conventional whole, chewable or dispersible tablets, dry syrups, suspension, sachets or any other suitable oral dosage form.

The taste masked pharmaceutical composition is prepared by reconstitution of the polymer coated drug particles in a liquid vehicle comprising sucrose, flavor and citric acid and a suspending agent like cellulose derivate or poly vinyl pyrrolidone or xanthan gum etc. The taste masked pharmaceutical composition of the present invention is made into liquid oral suspension by using the reconstitution medium of pH 4.5 comprising of sucrose, tutti-frutti flavor, citric acid and poly vinyl pyrrolidone.

The cefuroxime axetil to be incorporated in the pharmaceutical compositions will be preferably in the amorphous form. The amorphous form of the cefuroxime axetil is retained in the pharmaceutical compositions containing higher loading of the polymer having lower molecular weight. However it was observed that the low molecular weight polymers were not completely successful at lower loading in inhibition of the crystallization of cefuroxime axetil. The pH sensitive polymer of the present invention enhances the bioavailability of cefuroxime axetil, which can undergo gelation when brought in contact with the release medium. Release of cefuroxime axetil from the compositions is illustrated in examples 4-11 and example 16. Fast and almost complete release of cefuroxime axetil is assured as a result of inhibition of the gelation and crystallization of cefuroxime axetil in the pharmaceutical compositions. The release of the cefuroxime axetil with various loadings of the polymer as illustrated in the examples is shown in FIGS. 14 and 15. The X Ray Diffraction studies and DSC performed on the samples confirm the inhibition of crystallization. FIGS. 1, 2, 3 and 4 show the X ray diffraction pattern of the tray dried compositions as disclosed in the example 4 to 7.

FIGS. 5, 6,7, and 8 show the X ray diffraction pattern for co-precipitates obtained as disclosed in example 8 to 11. FIGS. 9, 10, 11 and 12 show the X ray diffraction pattern of the tray dried compositions as disclosed in the example 12 to 15. FIG. 13 shows the X ray diffraction pattern for the spray dried composition as disclosed in example 16.

When the polymer of higher molecular weight was used for formulation of the pharmaceutical compositions, cefuroxime axetil was maintained in substantially amorphous form both at lower polymeric loading. XRD studies and DSC performed on samples confirm the findings. Higher molecular weight polymers were successful in masking the taste and also in inhibiting the crystallization of cefuroxime axetil even at very low drug to polymer ratio.

Polymers of high molecular weight were used for the pharmaceutical compositions containing the drug celecoxib. The high molecular weight polymers maintained celecoxib in amorphous form even at higher and lower polymer loading. The polymers of all the molecular weight synthesized in the present invention can be applied for the taste masking of the pharmaceutical composition but with the polymers of high molecular weight the inhibition of crystallization of drug existing in amorphous form is achieved.

The present invention is illustrated by the following examples which are not intended to limit the scope of the invention in any manner. Taste masked pharmaceutical compositions exemplified in examples 4 to 11 and example 16 given below were tested for cefuroxime axetil release in 900 ml of 0.07 N hydrochloric acid, pH 1.3, at 37±0.5° C., using USP type II apparatus rotated at 100 rpm. Samples were withdrawn at 15, 30, 45, 60, 90, 120, 180 and 240 min. The amount withdrawn each time was replaced with fresh media to maintain the sink conditions. Dissolution results are given in respective tables for each example.

The taste masked pharmaceutical compositions as exemplified in the examples 12 to 15 given below, were tested for the celecoxib release in 100 ml of 0.1 N hydrochloric acid for 30 min and then the release was studied by addition of 900 ml of 0.1N NaOH, at 37±0.5° C., using USP type II apparatus rotated at 100 rpm. The samples were withdrawn at 15, 30, 45, 60, 90, 120, 180 and 240 min from 0.1N NaOH solution. The amount withdrawn each time was replaced with fresh media to maintain the sink conditions. The dissolution results are given in respective tables for each example.

EXAMPLE 4

1.5 g of Polymer of molecular weight 63,189 daltons and Cefuroxime axetil 3 g were dissolved in 40 ml of acetone containing 10% water. The resulting mixture was poured into a tray and dried at 27° C. under vacuum for 24 hours. The resulting drug polymer matrix was sized to obtain ASTM, mesh 40/60 particles. The drug release is indicated in the table 4

TABLE 4

| Time (min) | % Release |
|---|---|
| 15 | 42.0 |
| 30 | 47.0 |
| 60 | 52.5 |
| 90 | 56.9 |
| 120 | 59.6 |
| 180 | 62.0 |

EXAMPLE 5

4.050 g of Polymer of molecular weight 63,189 daltons and Cefuroxime axetil 1.350 g were dissolved in 40 ml of acetone containing 10% water. The resulting mixture was poured into a tray and dried at 27° C. under vacuum for 24 hours. The resulting drug polymer matrix was sized to obtain ASTM mesh 40/60 particles. The drug release is indicated in the Table 5

TABLE 5

| Time (min) | % Release |
|---|---|
| 15 | 94.84 |
| 30 | 98.0 |

EXAMPLE 6

1.5 g of Polymer with molecular weight 3,38,021 daltons and Cefuroxime axetil 3 g was dissolved in 50 ml of acetone containing 10% water. The resulting mixture was poured into a tray and dried at 27° C. under vacuum for 24 hours. The resulting drug polymer matrix was sized to obtain ASTM mesh 40/60 particles. The drug release is indicated in the Table 6

TABLE 6

| Time (min) | % Release |
|---|---|
| 15 | 72.36 |
| 30 | 91.17 |
| 45 | 92.48 |
| 60 | 93.58 |
| 90 | 97.30 |

The taste masked pharmaceutical composition of the particles prepared in example 6 is obtained by suspending the particles equivalent to 5 doses by using the reconstitution medium of pH 4.5 comprising of sucrose 85% w/v, tutti-frutti flavor qs., citric acid qs. and polyvinyl pyrrolidone 2%. Drug release during the storage for 7 days is shown in the Table 7.

TABLE 7

| Day | % Release |
|---|---|
| 2 | 2.33 |
| 3 | 3.81 |
| 4 | 3.99 |
| 5 | 4.28 |
| 6 | 5.44 |
| 7 | 6.63 |

EXAMPLE 7

4.050 g of polymer of molecular weight 3,38,021 daltons and Cefuroxime axetil 1.350 g were dissolved in 50 ml of acetone containing 10% water. The resulting mixture was poured into a tray at 27° C. under vacuum for 24 hours. The resulting drug polymer matrix was sized to obtain ASTM mesh 40/60 particles. Drug release is indicated in Table 8

TABLE 8

| Time (min) | % Release |
|---|---|
| 15 | 80.72 |
| 30 | 92.37 |
| 45 | 94.52 |
| 60 | 97.65 |

EXAMPLE 8

1.5 g of Polymer of molecular weight, 63,189 daltons and Cefuroxime axetil 3 g were dissolved in 40 ml of acetone containing 10% water. The resulting mixture was poured into petroleum ether maintained at 5° C. under stirring. The precipitate was separated and dried at 27° C. under vacuum for 24 hours. The resulting drug polymer matrix was sized to obtain ASTM mesh 40/60 particles. The drug release is indicated in the Table 9

TABLE 9

| Time (min) | % Release |
|---|---|
| 15 | 52.57 |
| 30 | 58.13 |
| 45 | 59.52 |
| 60 | 60.00 |
| 90 | 61.38 |
| 120 | 62.50 |
| 180 | 63.80 |

EXAMPLE 9

4.050 g of Polymer of molecular weight 63,189 daltons and Cefuroxime axetil 1.350 g were dissolved in 40 ml of acetone containing 10% water. The resulting mixture was poured into petroleum ether maintained at 5° C. under stirring. The precipitate was separated and dried at 27° C. under vacuum for 24 hours. The resulting drug polymer matrix was sized to obtain ASTM mesh 40/60 particles. The drug release is indicated in the Table 10

TABLE 10

| Time (min) | % Release |
|---|---|
| 15 | 85.29 |
| 30 | 91.61 |
| 45 | 94.40 |

EXAMPLE 10

1.5 g of Polymer with molecular weight 3,38,021 daltons and Cefuroxime axetil 3 g were dissolved in 50 ml of acetone containing 10% water. The resulting mixture was poured into petroleum ether maintained at 5° C. under stirring. The precipitate was separated and dried at 27° C. under vacuum for 24 hours. The resulting drug polymer matrix was sized to obtain ASTM mesh 40/60 particles. The drug release is indicated in Table 11.

TABLE 11

| Time (min) | % Release |
|---|---|
| 15 | 67.06 |
| 30 | 81.39 |
| 45 | 84.54 |
| 60 | 85.95 |
| 90 | 87.56 |
| 120 | 92.74 |
| 180 | 94.3 |

The taste masked pharmaceutical composition of the particles prepared in example 10 is obtained by suspending the particles equivalent to 5 doses by using the reconstitution medium of pH 4.5 comprising of sucrose 85% w/v, tutti-frutti flavor qs., citric acid qs. and polyvinyl pyrrolidone 2%. Drug release during the storage for 7 days is shown in Table 12

TABLE 12

| Day | % Release |
|---|---|
| 2 | 0.98 |
| 3 | 1.09 |
| 4 | 2.13 |
| 5 | 2.9 |
| 6 | 3.17 |
| 7 | 3.62 |

EXAMPLE 11

4.050 g of Polymer of molecular weight 3,38,021 daltons and Cefuroxime axetil 1.350 g were dissolved in 50 ml of acetone containing 10% water. The resulting mixture was poured into petroleum ether maintained at 5° C. under stirring. The precipitate was separated and dried at 27° C. under vacuum for 24 hours. The resulting drug polymer matrix was sized to obtain ASTM mesh 40/60 particles. The drug release is indicated in the table 13.

TABLE 13

| Time (min) | % Release |
|---|---|
| 15 | 64.75 |
| 30 | 74.89 |
| 45 | 79.40 |
| 60 | 80.54 |
| 90 | 85.80 |
| 120 | 90.30 |
| 180 | 93.70 |

EXAMPLE 12

0.75 g of Polymer of molecular weight 63,189 daltons and celecoxib 1.00 g were dissolved in 20 ml of Methanol-Dichloromethane (1.5:1). The resulting mixture was poured into a tray and dried at 27° C. under vacuum for 24 hours. The resulting drug polymer matrix was sized to obtain ASTM mesh 40/60 particles. The drug release is indicated in the table 14

TABLE 14

Example 12

| Time (min) | % Release |
|---|---|
| 15 | 76.76 |
| 30 | 85.50 |
| 60 | 92.10 |
| 90 | 95.14 |

EXAMPLE 13

1.8 g of Polymer of molecular weight 63,189 daltons and celecoxib 0.600 g were dissolved in 20 ml of Methanol-Dichloromethane (1.5:1). The resulting mixture was poured into a tray and dried at 27° C. under vacuum for 24 hours. The resulting drug polymer matrix was sized to obtain ASTM mesh 40/60 particles. The drug release is indicated in the table 15

TABLE 15

| Time (min) | % Release |
|---|---|
| 15 | 89.2 |
| 30 | 95.0 |

EXAMPLE 14

0.750 g of Polymer with molecular weight 2,72,177 daltons and Celecoxib 1.0 g were dissolved in 25 ml Methanol-Dichloromethane (1.5:1). The resulting mixture was poured into a tray and dried at 27° C. under vacuum for 24 hours. The resulting drug polymer matrix was sized to obtain ASTM mesh 40/60 particles. The drug release is indicated in the table 16

TABLE 16

| Time (min) | % Release |
|---|---|
| 15 | 93.4 |
| 30 | 96.2 |

EXAMPLE 15

1.8 g of Polymer with molecular weight 2,72,177 daltons and Celecoxib 0.600 g were dissolved in 35 ml Methanol-Dichloromethane (1.5:1). The resulting mixture was poured into a tray and dried at 27° C. under vacuum for 24 hours. The resulting drug polymer matrix was sized to obtain ASTM mesh 40/60 particles. The drug release is indicated in the table 17

TABLE 17

| Time (min) | % Release |
|---|---|
| 15 | 64.62 |
| 30 | 72.45 |
| 45 | 86.16 |
| 60 | 97.91 |

EXAMPLE 16

Cefuroxime axetil—polymer solution in the organic solvent was spray dried to obtain the taste masked micro particles. About 0.60 g polymer was dissolved in 30 ml solution of Methanol: Acetone: Dichloromethane (1:1:1). The polymer of molecular weight 2,72,177 and 1,25,280 each weighing 300 mg is used for the coating of cefuroxime axetil. To this, was added 2.4 g of Cefuroxime axetil and dissolved. The drying gas was air. The inlet air temperature to the spray dryer was in the range 40-70° C. The outlet air temperature was in the range of 25 to 50° C. The atomization was in the range of 1-2 kg. The feed rate was optimized from the range 20 to 85 rpm. The resulting solution was spray dried to obtain the taste masked micro particles. The drug release is indicated in the table 18.

TABLE 18

| Time (min) | % Release |
|---|---|
| 15 | 57.58 |
| 30 | 77.58 |
| 45 | 85.75 |
| 60 | 92.86 |

We claim:

1. A pharmaceutical composition comprising a pH sensitive polymer, which retards crystallization of a bitter drug exhibiting polymorphism, wherein the pH sensitive polymer has a molecular weight ranging from 50,000 to 700,000, the drug is present in substantially amorphous form within the polymer matrix, and the composition has a formula $$P[A_{(x)}B_{(y)}C_{(z)}]:D$$

wherein P is the pH sensitive polymer comprising a hydrophobic monomer A, a basic monomer B, and a hydrophilic monomer C; D is the bitter drug; X ranges from 30% to 95%, Y ranges from 50% to 70%, and Z ranges from 10% to 60% expressed in w/w; and polymer P to drug D has a ratio by weight ranging from 30:1 to 0.2:1.

2. The composition as claimed in claim 1 wherein the hydrophobic monomer A is comprised of derivatives of acrylic and methacrylic acid.

3. The composition as claimed in claim 2 wherein the acrylic acid derivative is selected from the group consisting of cyclohexyl acrylate, dodecyl acrylate, 2 ethyl hexyl acrylate, octyl acrylate, tertiary butyl acrylate, phenyl acrylate, and butyl acrylate.

4. The composition as claimed in claim 2 wherein the methacrylic acid derivative is selected from the group consisting of methyl methacrylate, benzyl methacrylate, cyclohexyl methacrylate, phenyl methacrylate, tertiary butyl methacrylate, butyl methacrylate, 2 ethyl hexyl methacrylate, and propyl methacrylate.

5. The composition as claimed in claim 1 wherein the basic monomer B comprises an alkenyl pyridine selected from the group consisting of 2-vinyl pyridine, 3-vinyl pyridine, 4-vinyl pyridine, 5-vinyl 2-picoline, 2-vinyl 4-picoline, 2-isopropenyl pyridine, and iso propenyl pyridine.

6. The composition as claimed in claim 5 wherein the basic monomer B comprises 4-vinyl pyridine.

7. The composition as claimed in claim 1 wherein the basic monomer B is selected from the group consisting of vinyl quinolines, aminoalkyl vinyl ethers, amino ethyl styrenes, and allylic amines.

8. The composition as claimed in claim 7 wherein the basic monomer B comprises an allylic amine.

9. The composition as claimed in claim 1 wherein the hydrophilic monomer C comprises a derivative of methacrylic acid selected from the group consisting of hydroxy ethyl methacrylate, hydroxy propyl methacrylate, and hydroxy ethoxy ethyl methacrylate.

10. The composition as claimed in claim 9 wherein the hydrophilic monomer C comprises hydroxy ethyl methacrylate or hydroxyl ethoxy ethyl methacrylate.

11. A pharmaceutical composition comprising a polymorphic drug in amorphous form selected from the group consisting of cephalosporin antibiotics, macrolide antibiotics, COX 2 inhibitors, nonsteroidal analgesic anti-inflammatory drugs, anti-histaminic drugs, and oxazolidinone antibiotics and a pH sensitive polymer of molecular weight ranging from 50,000 to 700,000 inhibiting recrystallization of drugs having a formula $$P[A_{(x)}B_{(y)}C_{(z)}]$$

wherein P is the pH sensitive polymer comprising a hydrophobic monomer A, a basic monomer B, and a hydrophilic monomer C; X ranges from 30% to 95%, Y ranges from 50% to 70%, and Z ranges from 10% to 60% expressed in w/w.

12. The composition as claimed in claim 11 wherein the drug comprises a cephalosporin antibiotic selected from the group consisting of cefuroxime axetil, cephalexin, cephadroxil, and cepfodoxime proxetil.

13. The composition as claimed in claim 11 wherein the drug comprises a COX 2 inhibitor selected from the group consisting of etoricoxib and celecoxib.

14. The composition as claimed in claim 11 wherein the drug comprises a macrolide antibiotic selected from the group consisting of clarithromycin, azithromycin, and erythromycin.

15. The composition as claimed in claim 11 wherein the drug comprises a nonsteroidal analgesic anti-inflammatory drug selected from the group consisting of ibuprofen, ketoprofen, acetaminophen, and indomethacin.

16. The composition as claimed in claim 11 wherein the drug comprises an anti-histaminic drug selected from the group consisting of famotidine and ranitidine.

17. The composition as claimed in claim 11 wherein the drug comprises oxazolidinone antibiotic linezolid.

18. The composition as claimed in claim 11 wherein weight of polymer to weight of drug has a ratio ranging from 30:1 to 0.2:1.

19. The composition as claimed in claim 18 wherein the polymer to drug ratio ranges from 5:1 to 0.4:1.

20. The composition as claimed in claim 11 wherein the polymer has a molecular weight ranging from 150,000 to 350,000.

21. The composition as claimed in claim 11 wherein the polymer comprises a blend of high molecular weight and low molecular weight polymers in the ratio 1:1 to 1:5 or 5:1 to 1:1 to effectively yield a polymer of molecular weight ranging from 150,000 to 350,000.

22. The composition as claimed in claim 11 formulated in solid dosage form as chewable, effervescent, or dispersible tablets.

23. The composition as claimed in claim 11 formulated in liquid dosage form as a dry syrup or suspension.

24. A pharmaceutical composition for retardation of crystallization rate produced by a process of microencapsulation, spray-drying, and fluid bed processing and the composition has a formula $$P[A_{(x)}B_{(y)}C_{(z)}]:D$$

wherein P is a pH sensitive polymer, A is a hydrophobic monomer, B is a basic monomer, C is a hydrophilic monomer, and D is a drug existing in polymorphic form; X ranges from 30% to 95%, Y ranges from 50% to 70%, and Z ranges from 10% to 65% expressed in w/w; and the process comprises dispersing the drug in a matrix formed by the polymer.

25. The composition as claimed in claim 24 wherein the drug dispersed in the polymer matrix is prepared by co-precipitation in a non solvent.

26. The composition as claimed in claim 24 wherein the drug dispersed in the polymer matrix is prepared by tray drying a solution of the drug and polymer.

27. The composition as claimed in claim 24 wherein the hydrophobic monomer comprises derivatives of acrylic and methacrylic acid.

28. The composition as claimed in claim 24 wherein the hydrophobic monomer comprises derivatives of acrylic acid selected from the group consisting of cyclohexyl acrylate, dodecyl acrylate, 2 ethyl hexyl acrylate, octyl acrylate, tertiary butyl acrylate, phenyl acrylate, and butyl acrylate.

29. The composition as claimed in claim 24 wherein the hydrophobic monomer comprises derivatives of methacrylic acid selected from the group consisting of methyl methacrylate, benzyl methacrylate, cyclohexyl methacrylate, phenyl methacrylate, tertiary butyl methacrylate, butyl methacrylate, 2 ethyl hexyl methacrylate, and propyl methacrylate.

30. The composition as claimed in claim 24 wherein the basic monomer comprises an alkenyl pyridine selected from the group consisting of 2-vinyl pyridine, 3-vinyl pyridine, 4-vinyl pyridine, 5-vinyl 2-picoline, 2-vinyl 4-picoline, 2 isopropenyl pyridine, and iso propenyl pyridine.

31. The composition as claimed in claim 30 wherein the basic monomer comprises 4-vinyl pyridine.

32. The composition as claimed in claim 24 wherein the basic monomer is selected from the group consisting of vinyl quinolines, aminoalkyl vinyl ethers, amino ethyl styrenes, and allylic amines.

33. The composition as claimed in claim 32 wherein the basic monomer comprises an allylic amine.

34. The composition as claimed in claim 24 wherein the hydrophilic monomer comprises derivatives of methacrylic acid selected from the group consisting of hydroxy ethyl methacrylate, hydroxy propyl methacrylate, and hydroxy ethoxy ethyl methacrylate.

35. The composition as claimed in claim 24 wherein the hydrophilic monomer comprises hydroxy ethyl methacrylate.

36. The composition as claimed in claim 24 wherein the hydrophilic monomer comprises hydroxy ethoxy ethyl methacrylate.

37. The composition as claimed in claim 24 wherein the drug is a cephalosporin antibiotic selected from the group consisting of cefuroxime, cephalexin, cephadroxil, and cepfodoxime proxetil.

38. The composition as claimed in claim 24 wherein the drug is a COX 2 inhibitor selected from the group consisting of etroricoxib and celecoxib.

39. The composition as claimed in claim 24 wherein the drug is a macrolide antibiotic selected from selected from the group consisting of clarithromycin, azithromycin, and erythromycin.

40. The composition as claimed in claim 24 wherein the drug is a nonsteroidal analgesic anti-inflammatory drug selected from the group consisting of ibuprofen, ketoprofen, acetaminophen, and indomethacin.

41. The composition as claimed in claim 24 wherein the drug is an anti-histaminic drug selected from the group consisting of famotidine and ranitidine.

42. The composition as claimed in claim 24 wherein the drug is oxazolidinone antibiotic linezolid.

* * * * *